United States Patent
MacNamara et al.

(10) Patent No.: US 12,018,232 B2
(45) Date of Patent: Jun. 25, 2024

(54) MULTILAYER DISSOLVABLE SOLID ARTICLE CONTAINING SOLID PARTICLES FOR MAKING THE SAME

(71) Applicant: The Procter & Gamble Company, Cincinnati, OH (US)

(72) Inventors: Carl David MacNamara, Beijing (CN); HongSing Tan, Beijing (CN); Robert Wayne Glenn, Jr., Singapore (SG); Wenhu Pang, Beijing (CN); Kejing Du, Beijing (CN); Yuxiang Liu, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/482,488

(22) Filed: Sep. 23, 2021

(65) Prior Publication Data
US 2022/0112449 A1   Apr. 14, 2022

(30) Foreign Application Priority Data

Oct. 9, 2020 (WO) ................ PCT/CN2020/119952

(51) Int. Cl.
| | |
|---|---|
| *C11D 17/04* | (2006.01) |
| *C11D 1/14* | (2006.01) |
| *C11D 1/22* | (2006.01) |
| *C11D 3/00* | (2006.01) |
| *C11D 3/20* | (2006.01) |
| *C11D 3/37* | (2006.01) |
| *C11D 3/386* | (2006.01) |
| *C11D 3/39* | (2006.01) |
| *C11D 3/395* | (2006.01) |

(Continued)

(52) U.S. Cl.
CPC ............ *C11D 17/044* (2013.01); *C11D 1/146* (2013.01); *C11D 1/22* (2013.01); *C11D 3/0052* (2013.01); *C11D 3/2086* (2013.01); *C11D 3/3917* (2013.01); *C11D 11/0082* (2013.01)

(58) Field of Classification Search
None
See application file for complete search history.

(56) References Cited

U.S. PATENT DOCUMENTS

| | | | |
|---|---|---|---|
| 4,170,565 A | 10/1979 | Flesher et al. | |
| 4,483,778 A * | 11/1984 | Thompson | ............ C07C 309/00 252/186.25 |

(Continued)

FOREIGN PATENT DOCUMENTS

| | | |
|---|---|---|
| CA | 1242949 A | 10/1988 |
| CN | 1202517 A | 12/1998 |

(Continued)

OTHER PUBLICATIONS

PCT Search Report and Written Opinion for PCT/CN2020/119952 dated Jul. 13, 2021, 9 pages.

(Continued)

*Primary Examiner* — Lorna M Douyon
(74) *Attorney, Agent, or Firm* — Andrew J. Mueller

(57) ABSTRACT

A dissolvable solid article which can include multiple layers of flexible, dissolvable, porous sheets, in which a coating composition including solid particles is present on at least one internal surface of at least one sheet and a process for making such solid articles.

20 Claims, 7 Drawing Sheets

(51) Int. Cl.
   *C11D 11/00*   (2006.01)
   *C11D 17/06*   (2006.01)

(56)   References Cited

U.S. PATENT DOCUMENTS

| | | | |
|---|---|---|---|
| 4,557,852 | A | 12/1985 | Schulz et al. |
| 4,610,799 | A | 9/1986 | Wilsberg et al. |
| 4,654,395 | A | 3/1987 | Schulz et al. |
| 4,743,394 | A | 5/1988 | Kaufmann et al. |
| 4,747,976 | A | 5/1988 | Yang et al. |
| 4,806,261 | A | 2/1989 | Ciallella et al. |
| 4,938,888 | A | 7/1990 | Kiefer et al. |
| 5,202,045 | A | 4/1993 | Karpusiewicz et al. |
| 6,130,193 | A * | 10/2000 | Gillette ............... C11D 17/046 510/438 |
| 6,465,407 | B2 | 10/2002 | Hayashi |
| 6,699,826 | B1 | 3/2004 | Saijo |
| 6,818,606 | B1 | 11/2004 | Hanada |
| 7,094,744 | B1 | 8/2006 | Kobayashi |
| 8,367,596 | B2 | 2/2013 | Fossum et al. |
| 2002/0091169 | A1 | 7/2002 | Klotzer |
| 2006/0252667 | A1 | 11/2006 | Mort, III et al. |
| 2009/0104420 | A1 | 4/2009 | Nadella et al. |
| 2010/0173817 | A1* | 7/2010 | Glenn, Jr. ............ A61K 8/731 510/120 |
| 2011/0027328 | A1* | 2/2011 | Baig .................... A61K 8/8129 424/49 |
| 2011/0136719 | A1 | 6/2011 | Jalbert |
| 2015/0159330 | A1 | 6/2015 | Weisman et al. |
| 2015/0218497 | A1 | 8/2015 | Jalbert et al. |
| 2015/0291913 | A1 | 10/2015 | Tan et al. |
| 2015/0313808 | A1* | 11/2015 | Lynch ................. A61K 8/34 510/119 |
| 2020/0308517 | A1* | 10/2020 | Tan .......................... B32B 3/02 |
| 2021/0121373 | A1* | 4/2021 | Tan ..................... A61K 8/365 |
| 2021/0261892 | A1* | 8/2021 | Xu ...................... A61Q 19/10 |
| 2021/0332312 | A1 | 10/2021 | Tan et al. |
| 2022/0054365 | A1* | 2/2022 | Xu ........................ C11D 17/06 |

FOREIGN PATENT DOCUMENTS

| | | |
|---|---|---|
| CN | 2352536 Y | 12/1999 |
| CN | 1250085 A | 4/2000 |
| CN | 1421519 A | 6/2003 |
| CN | 1583991 A | 2/2005 |
| CN | 102492573 A | 6/2012 |
| CN | 202744521 U | 2/2013 |
| CN | 202754982 U | 2/2013 |
| CN | 102732392 B | 9/2013 |
| CN | 102965223 B | 1/2014 |
| CN | 103608448 A | 2/2014 |
| CN | 103740490 A | 4/2014 |
| CN | 105199887 A | 12/2015 |
| CN | 105238584 A | 1/2016 |
| CN | 105462733 A | 4/2016 |
| CN | 105586165 A | 5/2016 |
| CN | 105602773 A | 5/2016 |
| CN | 105647716 A | 6/2016 |
| CN | 205398584 U | 7/2016 |
| CN | 105861168 A | 8/2016 |
| CN | 105886142 A | 8/2016 |
| CN | 205420320 U | 8/2016 |
| CN | 106635572 A | 5/2017 |
| EP | 0234867 B1 | 1/1993 |
| JP | S5974198 A | 4/1984 |
| JP | 63012466 A | 1/1988 |
| JP | 63150396 A | 6/1988 |
| JP | H04202600 A | 7/1992 |
| JP | 63008496 A | 7/2006 |
| JP | 4509284 B2 | 5/2010 |
| JP | 2012501372 A | 1/2012 |
| KR | 20080111815 A | 12/2008 |
| KR | 20090036882 A | 4/2009 |
| KR | 20090036883 A | 4/2009 |
| KR | 20100090122 A | 8/2010 |
| KR | 20100096985 A | 9/2010 |
| KR | 101146292 B1 | 5/2012 |
| KR | 20120127174 A | 11/2012 |
| KR | 20120130693 A | 12/2012 |
| WO | 2009095891 A1 | 8/2009 |
| WO | 2009129358 A2 | 10/2009 |
| WO | 2010077627 A2 | 7/2010 |
| WO | 2010077628 A2 | 7/2010 |
| WO | 2010135238 A1 | 11/2010 |
| WO | 2011014643 A1 | 2/2011 |
| WO | 2011071965 A2 | 6/2011 |
| WO | 2012138820 A1 | 10/2012 |
| WO | 2012157851 A2 | 11/2012 |
| WO | 2014059252 A2 | 4/2014 |
| WO | 2017105131 A1 | 6/2017 |
| WO | WO 2021/077369 A1 * | 10/2019 |
| WO | 2020123888 A1 | 6/2020 |
| WO | 2020191577 A1 | 10/2020 |
| WO | WO 2021/077369 A1 * | 4/2021 |

OTHER PUBLICATIONS

PCT Suppl. Search Report and Written Opinion for PCT/CN2020/119952 dated Jan. 4, 2023, 06 pages.

* cited by examiner (Laundry Impingement Oven)

(Laundry Drum)

MULTILAYER DISSOLVABLE SOLID ARTICLE CONTAINING SOLID PARTICLES FOR MAKING THE SAME

FIELD OF THE INVENTION

The present disclosure relates to multilayer dissolvable solid articles containing solid particles and a process for making the same.

BACKGROUND OF THE INVENTION

Flexible dissolvable sheets comprising surfactant(s) and/or other active ingredients in a water-soluble polymeric carrier or matrix are well known. Such sheets are particularly useful for delivering surfactants and/or other active ingredients upon dissolution in water. In comparison with traditional granular or liquid forms in the same product category, such sheets have better structural integrity, are more concentrated and easier to store, ship/transport, carry, and handle. In comparison with the solid tablet form in the same product category, such sheets are more flexible and less brittle, with better sensory appeal to the consumers.

To improve dissolution profile of such sheets, some studies has developed porous sheets with open-celled foam (OCF) structures characterized by a Percent Open Cell Content of from about 80% to 100%. Particularly, WO2010077627 discloses a batch process for forming such porous sheets with OCF structures that comprises vigorously aerating a pre-mixture of raw materials and then allowing the aerated pre-mixture to be heat-dried in batches (e.g., in a convection oven or a microwave oven) to form the porous sheets with the desired OCF structures. WO2012138820 discloses a similar process as that of WO2010077627, except that continuous drying of the aerated wet pre-mixture is achieved by using, e.g., an impingement oven (instead of a convection oven or a microwave oven).

On the other hand, in order to deliver a sufficient amount of surfactant(s) and/or other active ingredients to achieve desired product functions, it is desirable to use multiple layers of such flexible and dissolvable sheets, and it is further desirable to assemble such multiple layers into a unitary dissolvable solid article, which can then be sold as a unitary finished product. Furthermore, some active ingredients that are not suitable for processing into the sheets due to thermal stability or deactivation upon contact with water may be applied as a coating composition between layers of the multi-layer article. Such coating composition containing active ingredients applied between layers in the multi-layer article may be in a liquid form or a particulate form. However, various challenges may be encountered when trying to apply such coating composition between the sheets. Particularly, some active ingredients (e.g. bleaching agents, effervescent systems and the like) only exists in the form of solid particles but incorporating these particles between layers of foam includes significant challenges. For example, sealing particles between layers of foam sheets is technically challenging (i.e., the presence of solid particles might bring about insufficient contact area between adjacent layers to enable good sealing or particles at the edge might prevent sealing in that area and leave the side of the product open) and may cause powder leakage upon usage which is undesirable for consumers.

Therefore, there is a continuing need for a multi-layer article containing solid particles composition with improved performance.

SUMMARY OF THE INVENTION

Described herein is a coating composition comprising solid particles dispersed in a non-aqueous liquid carrier applied on one or both contacting surfaces of adjacent layers of the multilayer flexible, dissolvable, porous sheets to provide a multi-layer article with improved performance.

The inventors found that solid particles are often incompatible with the non-aqueous liquid carrier. The solid particles tend to aggregate and/or sediment. In some worse cases, phase separation occurs. To solve this problem, the present inventors developed a coating composition comprising a non-aqueous liquid carrier, a thickening agent, and solid particles. Particularly, the coating composition can comprise a nonionic surfactant as a non-aqueous liquid carrier, a thickening agent, and solid particles. In some examples, the thickening agent may be selected from the group consisting of silica, clays, polyacrylate thickeners, polyacrylamide thickeners, xanthan thickeners, guar gum, alginates ethoxylated cellulose, hydroxy propyl cellulose, hydroxy ethyl cellulose, and any combinations thereof.

The inventors surprisingly found the coating composition may have significantly improved stability. Additionally, the coating composition may provide additional benefits including but not limited to improved stability of active ingredients, improved leakage, improved loading capability, and improved process feasibility. Particularly, the inventors surprisingly found that the stability of bleaching agents added as the solid particles in the coating composition is significantly improved. Such improvement is completely unexpected, in view that the porous structure of the multi-layer dissolvable solid article allows air or moisture to enter and in other words, the bleaching agents between layers can still come into contact with environmental substances.

The description herein includes a dissolvable solid article comprising two or more flexible, porous, dissolvable sheets, wherein each of the two or more sheets comprises a water-soluble polymer and a surfactant and is characterized by a Percent Open Cell Content of from 80% to 100% and an Overall Average Pore Size of from 100 m to 2000 m; and wherein a coating composition comprising a non-aqueous liquid carrier, solid particles and a thickening agent is present on at least one surface of at least one of the two or more sheets, provided that the coating composition is not on any of the outer surfaces of the dissolvable solid article. The solid particles can comprise a first group of particles and a second group of particles in which the first group of particles comprises a source of available oxygen that can be selected from the group consisting of percarbonate salts, perborate salts, persulfate salts, and any combinations thereof and the second group of particles comprises a bleach activator is selected from the group consisting of tetraacetylethylenediamine (TAED), oxybenzene sulphonates, caprolactams; pentaacetate glucose (PAG), nitrile quaternary ammonium, imide bleach activators, and any combinations thereof.

In another aspect, a dissolvable solid article can comprise three or more flexible, porous, dissolvable sheets, wherein each of the three or more sheets comprises a water-soluble polymer and a surfactant and is characterized by a Percent Open Cell Content of from 80% to 100% and an Overall Average Pore Size of from 100 μm to 2000 μm; wherein a first coating composition is present on at least one surface of at least one of the three or more sheets in which the first coating composition comprises a first non-aqueous liquid carrier, a thickening agent, and a first group of solid particles comprising a source of available oxygen; wherein a second coating composition is present on at least one surface of at least one of the three or more sheets in which the second coating composition comprises a second non-aqueous liquid carrier, a thickening agent, and a second group of solid particles comprising a bleach activator, wherein the first non-aqueous liquid carrier and the second non-aqueous liquid carrier are independently selected from the group consisting of polyethylene glycol, polypropylene glycol, silicone, fatty acid, perfume oil, a non-ionic surfactant and any combinations thereof; provided that the first and second coating compositions are not on the same surface and are not on any of the outer surfaces of the dissolvable solid article. The first coating composition may comprise from 20% to 50% of the first non-aqueous liquid carrier which is $C_6$-$C_{20}$ linear or branched alkylalkoxylated alcohols (AA) having a weight average degree of alkoxylation ranging from 5 to 15, from 30% to 70% of the first group of solid particles comprising percarbonate salts or perborate salts and from 0.1% to 1.5% of the thickening agent; and wherein the second coating composition may comprise from 20% to 50% of the second non-aqueous liquid carrier which is a $C_6$-$C_{20}$ linear or branched alkylalkoxylated alcohols (AA) having a weight average degree of alkoxylation ranging from 5 to 15, from 30% to 70% of the second group of solid particles comprising tetraacetylethylenediamine (TAED) and from 0.1% to 1.5% of the thickening agent.

In a further aspect, a process for preparing a dissolvable solid article can comprise the steps of: 1) providing two or more flexible, porous, dissolvable sheets and a coating composition, wherein each of said two or more sheets comprises a water-soluble polymer and a surfactant and is characterized by a Percent Open Cell Content of from 80% to 100% and an Overall Average Pore Size of from 100 μm to 2000 μm, and wherein said coating composition comprises a non-aqueous liquid carrier, solid particles and a thickening agent; 2) applying the coating composition on at least one surface of at least one sheet from said two or more sheets; and 3) arranging the two or more sheets into a stack to form the dissolvable solid article so that the coating composition is not on any of the outer surfaces of the stack. The two or more flexible, porous, dissolvable sheets may be provided by using the following steps: a) preparing a wet pre-mixture comprising said water-soluble polymer and said surfactant; b) aerating said wet pre-mixture to form an aerated wet pre-mixture; c) forming said aerated wet pre-mixture into a sheet having opposing first and second sides; and d) drying said formed sheet to make said two or more flexible, porous, dissolvable sheet. The step d) may be conducted for a duration from 5 min to 300 min, from 10 min to 120 min, at a temperature from 70° C. to 200° C., or from 90° C. to 140° C., along a heating direction that forms a temperature gradient decreasing from the first side to the second side of the formed sheet, wherein the heating direction is substantially opposite to the gravitational direction for more than half of the drying time, or for more than 75% of the drying time. Particularly, the wet pre-mixture may have a viscosity of from 1,000 cps to 25,000 cps measured at 40° C. and 1 s-1, and/or the aerated wet pre-mixture may have a density of from 0.05 to 0.7 g/ml, from 0.15 g/ml to 0.6 g/ml, from 0.2 g/ml to 0.5 g/ml, or from 0.25 g/ml to 0.45 g/ml.

In a further aspect, the present invention is related to use of the dissolvable solid article according to the present disclosure in removing bacteria and/or malodor prevention or reduction.

It is an advantage of the dissolvable solid article according to the present disclosure that the coating composition with a thickening agent shows a significantly improved stability compared to the coating composition without a thickening agent.

It is an advantage of the dissolvable solid article according to the present disclosure that the dissolvable solid article may contain a sufficient amount of active ingredients as solid particles for delivering the benefit. In other words, the dissolvable solid article according to the present disclosure provides a carrier having an enhanced capability for loading solid particles. Particularly, the dissolvable solid article containing the coating composition with a thickening agent may result in less leakage compared to the dissolvable solid article containing the coating composition without a thickening agent when loading the same amount of solid particles, i.e. it provides a balance between the dissolution profile and the leakage.

It is an advantage of the dissolvable solid article according to the present disclosure that the moisture-sensitive active ingredients (e.g. a bleaching agent) contained in the dissolvable solid article shows a significantly improved stability compared to the moisture-sensitive active ingredients alone stored under the same condition. In other words, the dissolvable solid article according to the present disclosure provides a better environment for the storage of the moisture-sensitive active ingredients.

It is an advantage of the dissolvable solid article according to the present disclosure that it may provide a perfect carrier for bleaching agents (e.g. the source of available oxygen and the bleach activator). Particularly, the source of available oxygen and the bleach activator in the dissolvable solid article may be present in a physically separate manner to prevent a premature reaction therebetween when accidentally coming into contact with water or moisture. More particularly, the dissolvable solid article may be formed into a multilayer structure having an improved dissolution rate, in which the source of available oxygen and the bleach activator may be separately applied between two adjacent layers (i.e., the source of available oxygen is applied between two adjacent layers and the bleach activator is applied between another two adjacent layers).

It is an advantage of the dissolvable solid article according to the present disclosure that it may achieve an excellent anti-microorganism effect. Particularly, the dissolvable solid article according to the present disclosure may significantly remove microorganism from fabrics or hard surfaces (for example glass, wood, metal, ceramic and the like). In the context of the present disclosure, removing microorganism includes but not limited to kill, deactivate, eliminate and/or wash away microorganism.

It is an advantage of the dissolvable solid article according to the present disclosure that it may achieve an excellent malodor prevention or reduction.

These and other aspects of the present invention will become more apparent upon reading the following detailed description of the invention.

DETAILED DESCRIPTION OF THE INVENTION

I. Definitions

Figure 1:
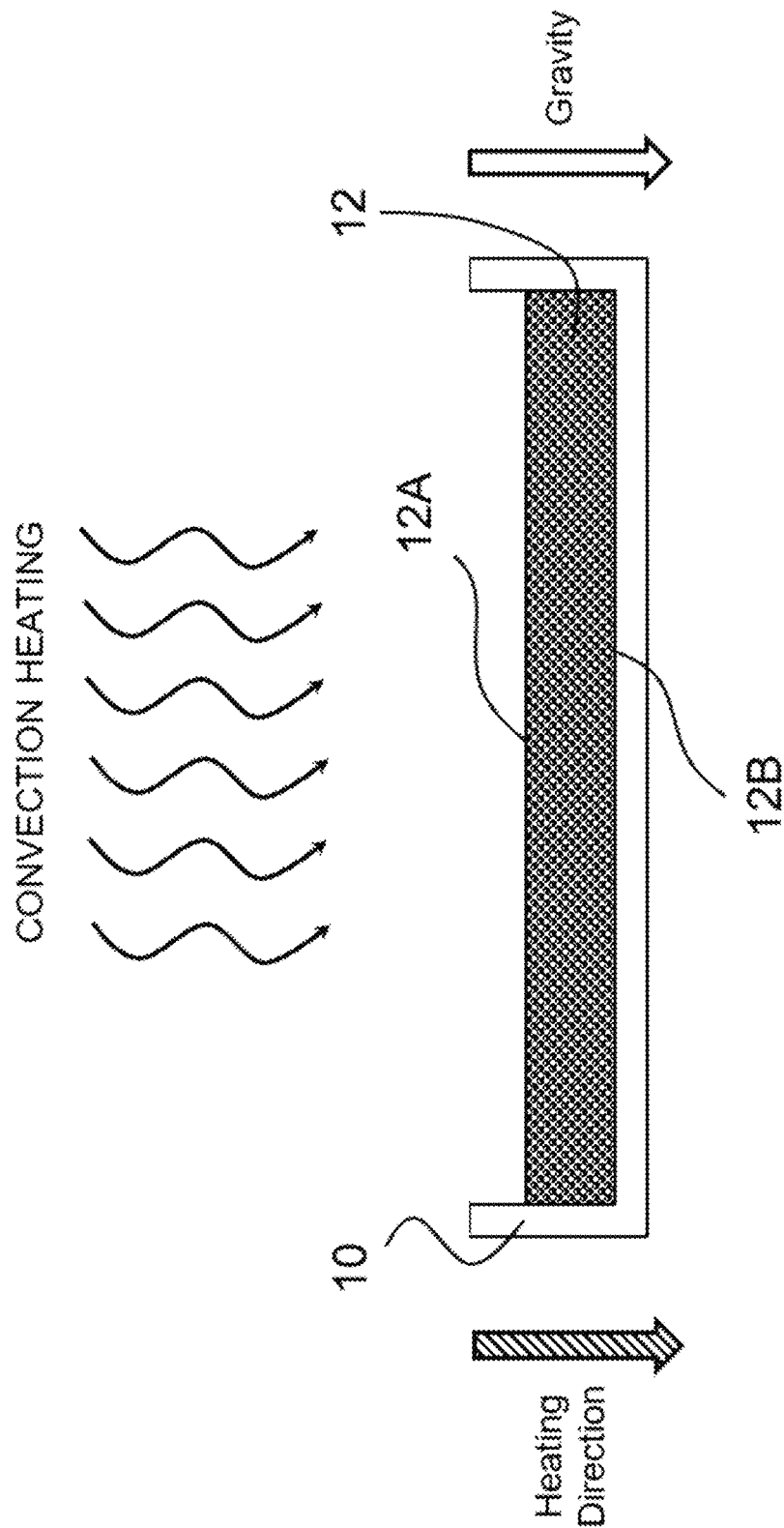
FIG. 1 shows a convection-based heating/drying arrangement for making a flexible, porous, dissolvable solid sheet article in a batch process.

The term "flexible" as used herein refers to the ability of an article to withstand stress without breakage or significant fracture when it is bent at 90° along a center line perpendicular to its longitudinal direction. The article can undergo significant elastic deformation and is characterized by a Young's Modulus of no more than 5 GPa.

The term "dissolvable" as used herein refers to the ability of an article to completely or substantially dissolve in a sufficient amount of deionized water at 20° C. and under the atmospheric pressure within eight (8) hours without any stirring, leaving less than 5 wt % undissolved residues.

The term "solid" as used herein refers to the ability of an article to substantially retain its shape (i.e., without any visible change in its shape) at 20° C. and under the atmospheric pressure, when it is not confined and when no external force is applied thereto.

The term "sheet" as used herein refers to a non-fibrous structure having a three-dimensional shape, i.e., with a thickness, a length, and a width, while the length-to-thickness aspect ratio and the width-to-thickness aspect ratio are both at least about 5:1, and the length-to-width ratio is at least about 1:1. The length-to-thickness aspect ratio and the width-to-thickness aspect ratio can both at least be about 10:1, at least about 15:1, at least about 20:1; and the length-to-width aspect ratio can be at least about 1.2:1, at least about 1.5:1, or at least about 1.618:1.

The term "contacting surfaces" of adjacent sheets as used herein refers two surfaces that are contacting with each other when the adjacent sheets are arranged in a stack, in which the two surfaces are respectively from the two adjacent sheets. For example, the contacting surfaces may be a lower surface of an upper sheet and an upper surface of a lower sheet if the two adjacent sheets are vertically arranged as a stack.

As used herein, the term "bottom surface" refers to a surface of the flexible, porous, dissolvable solid sheet that is immediately contacting a supporting surface upon which the sheet of aerated wet pre-mixture is placed during the drying step, while the term "top surface" refers to a surface of the sheet that is opposite to the bottom surface. Further, such solid sheet can be divided into three (3) regions along its thickness, including a top region that is adjacent to its top surface, a bottom region that is adjacent to its bottom surface, and a middle region that is located between the top and bottom regions. The top, middle, and bottom regions are of equal thickness, i.e., each having a thickness that is about ⅓ of the total thickness of the sheet.

As used herein, the term "outermost sheet" refers to a sheet that is adjacent to only one sheet in the multilayer dissolvable solid article.

The term "open celled foam" or "open cell pore structure" as used herein refers to a solid, interconnected, polymer-containing matrix that defines a network of spaces or cells that contain a gas, typically a gas (such as air), without collapse of the foam structure during the drying process, thereby maintaining the physical strength and cohesiveness of the solid. The interconnectivity of the structure may be described by a Percent Open Cell Content, which is measured by Test 3 disclosed hereinafter.

The term "water-soluble" as used herein refers to the ability of a sample material to completely dissolve in or disperse into water leaving no visible solids or forming no visibly separate phase, when at least about 25 grams, of such material is placed in one liter (1 L) of deionized water at 20° C. and under the atmospheric pressure with sufficient stirring.

The term "aerate", "aerating" or "aeration" as used herein refers to a process of introducing a gas into a liquid or pasty composition by mechanical and/or chemical means.

The term "heating direction" as used herein refers to the direction along which a heat source applies thermal energy to an article, which results in a temperature gradient in such article that decreases from one side of such article to the other side. For example, if a heat source located at one side of the article applies thermal energy to the article to generate a temperature gradient that decreases from the one side to an opposing side, the heating direction is then deemed as extending from the one side to the opposing side. If both sides of such article, or different sections of such article, are heated simultaneously with no observable temperature gradient across such article, then the heating is carried out in a non-directional manner, and there is no heating direction.

The term "substantially opposite to" or "substantially offset from" as used herein refers to two directions or two lines having an offset angle of 90° or more therebetween.

The term "substantially aligned" or "substantial alignment" as used herein refers to two directions or two lines having an offset angle of less than 90° therebetween.

The term "primary heat source" as used herein refers to a heat source that provides more than 50%, more than 60%, more than 70%, or more than 80%, of the total thermal energy absorbed by an object (e.g., the sheet of aerated wet pre-mixture according to the present invention).

The term "controlled surface temperature" as used herein refers to a surface temperature that is relatively consistent, i.e., with less than +/−20% fluctuations, less than +/−10% fluctuations, or less than +/−5% fluctuations.

The term "essentially free of" or "essentially free from" means that the indicated material is not deliberately added to the composition or product, or not present at an analytically detectable level in such composition or product. It may include compositions or products in which the indicated material is present only as an impurity of one or more of the materials deliberately added to such compositions or products.

II. Overview of Processes for Making Solid Sheets

WO2010077627 discloses a batch process for forming porous sheets with open-celled foam (OCF) structures characterized by a Percent Open Cell Content of from about 80% to 100%, which functions to improve dissolution. Specifically, a pre-mixture of raw materials is first formed, which is vigorously aerated and then heat-dried in batches (e.g., in a convection oven or a microwave oven) to form the porous sheets with the desired OCF structures. Although such OCF structures significantly improve the dissolution rate of the resulting porous sheets, there is still a visibly denser and less porous bottom region with thicker cell walls in such sheets. Such high-density bottom region may negatively impact the flow of water through the sheets and thereby may adversely affect the overall dissolution rate of the sheets. When a plurality of such sheets is stacked together to form a multilayer structure, the "barrier" effect of multiple high-density bottom regions is especially augmented.

WO2012138820 discloses a similar process as that of WO2010077627, except that continuous drying of the aerated wet pre-mixture is achieved by using, e.g., an impingement oven (instead of a convection oven or a microwave oven). The OCF sheets formed by such a continuous drying process are characterized by improved uniformity/consistency in the pore structures across different regions thereof. Unfortunately, there are still rate-limiting factors in such OCF sheets, such as a top surface with relatively smaller pore openings and a top region with relatively smaller pores (i.e., a crust-like top region), which may negatively impact the flow of water therethrough and slow down the dissolution thereof.

During the drying step in the above-described processes, the OCF structures are formed under simultaneous mechanisms of water evaporation, bubble collapse, interstitial liquid drainage from the thin film bubble facings into the plateau borders between the bubbles (which generates openings between the bubbles and forms the open cells), and solidification of the pre-mixture. Various processing conditions may influence these mechanisms, e.g., solid content in the wet pre-mixture, viscosity of the wet pre-mixture, gravity, and the drying temperature, and the need to balance such processing conditions so as to achieve controlled drainage and form the desired OCF structures.

It has been a surprising and unexpected discovery by the inventors that the direction of thermal energy employed (i.e., the heating direction) during the drying step may also have a significant impact on the resulting OCF structures, in addition to the above-mentioned processing conditions.

For example, if the thermal energy is applied in a non-directional matter (i.e., there is no clear heating direction) during the drying step, or if the heating direction is substantially aligned with the gravitational direction (i.e., with an offset angle of less than 90° in between) during most of the drying step, the resulting flexible, porous, dissolvable solid sheet tends to have a top surface with smaller pore openings and greater pore size variations in different regions along the direction across its thickness. In contrast, when the heating direction is offset from the gravitation direction (i.e., with an offset angle of 90° or more therebetween) during most of the drying step, the resulting solid sheet may have a top surface with larger pore openings and reduced pore size variations in different regions along the direction across the thickness of such sheet. Correspondingly, the latter sheets are more receptive to water flowing through and are therefore more dissolvable than the former sheets.

While not being bound by any theory, it is believed that the alignment or misalignment between the heating direction and the gravitational direction during the drying step and the duration thereof may significantly affect the interstitial liquid drainage between the bubbles, and correspondingly impacting the pore expansion and pore opening in the solidifying pre-mixture and resulting in solid sheets with very different OCF structures. Such differences are illustrated more clearly by FIGS. 1-4 hereinafter.

FIG. 1 shows a convection-based heating/drying arrangement. During the drying step, a mold 10 (which can be made of any suitable materials, such as metal, ceramic or Teflon®) is filled with an aerated wet pre-mixture, which forms a sheet 12 having a first side 12A (i.e., the top side) and an opposing second side 12B (i.e., the bottom side since it is in direct contact with a supporting surface of the mold 10). Such mold 10 is placed in a 130° C. convection oven for approximately 45-46 minutes during the drying step. The convection oven heats the sheet 12 from above, i.e., along a downward heating direction (as shown by the cross-hatched arrowhead), which forms a temperature gradient in the sheet 12 that decreases from the first side 12A to the opposing second side 12B. The downward heating direction is aligned with gravitational direction (as shown by the white arrowhead), and such an aligned position is maintained throughout the entire drying time. During drying, gravity drains the liquid pre-mixture downward toward the bottom region, while the downward heating direction dries the top region first and the bottom region last. As a result, a porous solid sheet is formed with a top surface that contains numerous pores with small openings formed by gas bubbles that have not had the chance to fully expand. Such a top surface with smaller pore openings is not optimal for water ingress into the sheet, which may limit the dissolution rate of the sheet. On the other hand, the bottom region of such sheet is dense and less porous, with larger pores that are formed by fully expanded gas bubbles, but which are very few in numbers, and the cell walls between the pores in such bottom region are thick due to the downward liquid drainage effectuated by gravity. Such a dense bottom region with fewer pores and thick cell walls is a further rate-limiting factor for the overall dissolution rate of the sheet.

Figure 2:
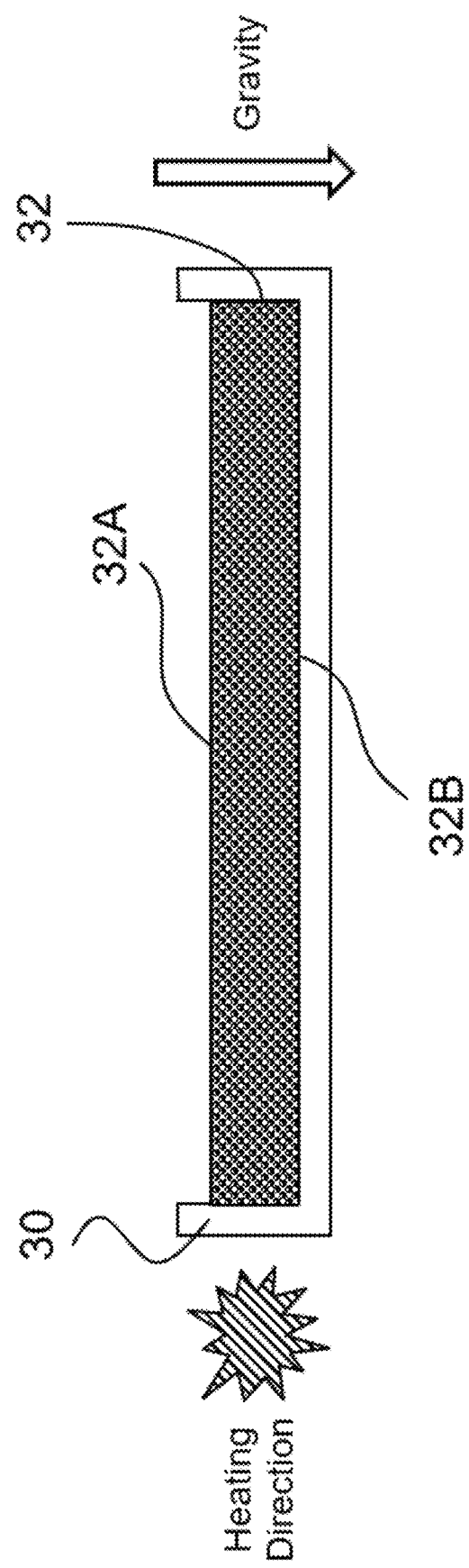
FIG. 2 shows a microwave-based heating/drying arrangement for making a flexible, porous, dissolvable solid sheet article in a batch process.

FIG. 2 shows a microwave-based heating/drying arrangement. During the drying step, a mold 30 is filled with an aerated wet pre-mixture, which forms a sheet 32 having a first side 32A (the top side) and an opposing second side 32B (the bottom side). Such mold 30 is then placed in a low energy density microwave applicator (not shown), which is provided by Industrial Microwave System Inc., North Carolina and operated at a power of 2.0 kW, a belt speed of 1 foot per minute and a surrounding air temperature of 54.4° C. The mold 30 is placed in such microwave application for approximately 12 minutes during the drying step. Such microwave applicator heats the sheet 32 from within, without any clear or consistent heating direction. Correspondingly, no temperature gradient is formed in the sheet 32. During drying, the entire sheet 32 is simultaneously heated, or nearly simultaneously heated, although gravity (as shown by the white arrowhead) still drains the liquid pre-mixture downward toward the bottom region. As a result, the solidified sheet so formed has more uniformly distributed and more evenly sized pores, in comparison with sheet formed by the convection-based heating/drying arrangement. However, the liquid drainage under gravity force during the microwave-based drying step may still result in a dense bottom region with thick cell walls. Further, simultaneous heating of the entire sheet 32 may still limit the pore expansion and pore opening on the top surface during the drying step, and the resulting sheet may still have a top surface with relatively smaller pore openings. Further, the microwave energy heats water within the sheet 32 and causes such water to boil, which may generate bubbles of irregular sizes and form unintended dense regions with thick cell walls.

Figure 3:
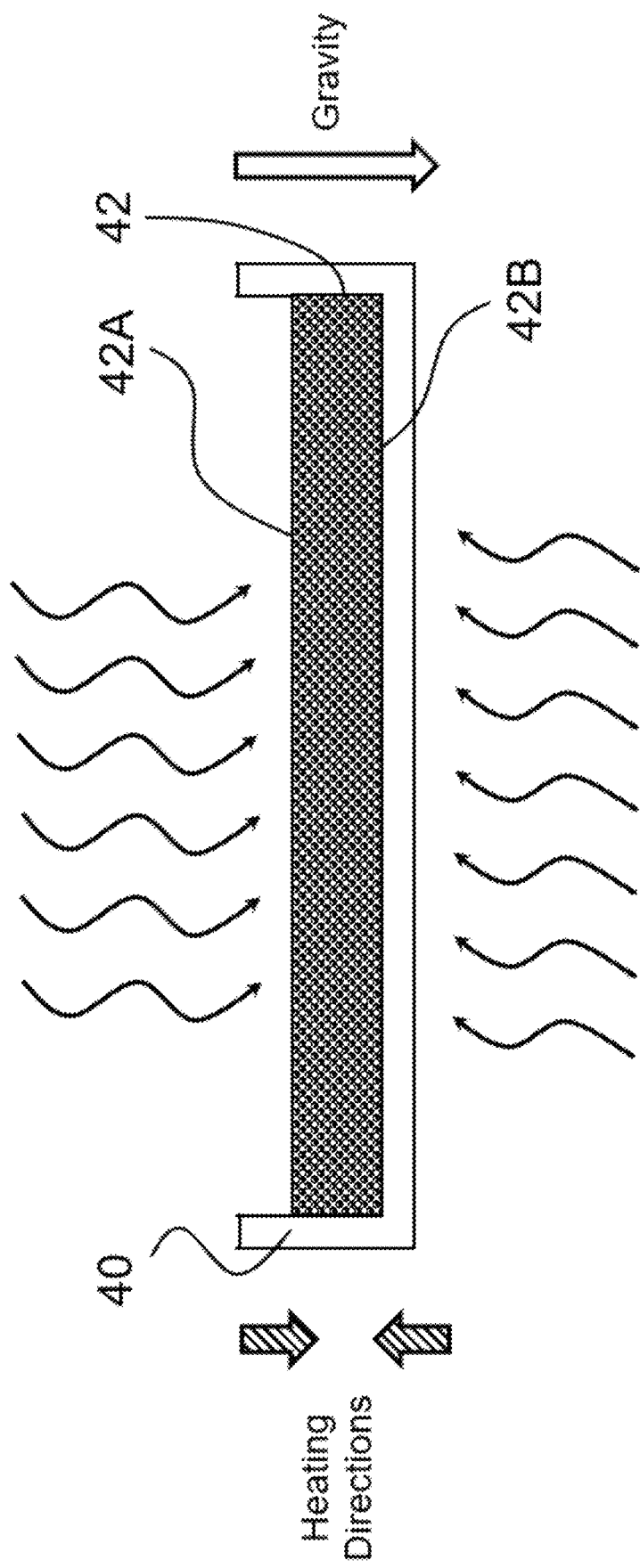
FIG. 3 shows an impingement oven-based heating/drying arrangement for making a flexible, porous dissolvable solid sheet article in a continuous process.

FIG. 3 shows an impingement oven-based heating/drying arrangement. During the drying step, a mold 40 is filled with an aerated wet pre-mixture, which forms a sheet 42 having a first side 42A (the top side) and an opposing second side 42B (the bottom side). Such mold 40 is then placed in a continuous impingement oven (not shown) under conditions similar to those described in Example 1, Table 2 of WO2012138820. Such continuous impingement oven heats the sheet 42 from both top and bottom at opposing and offsetting heating directions (shown by the two cross-hatched arrowheads). Correspondingly, no clear temperature gradient is formed in the sheet 42 during drying, and the entire sheet 42 is nearly simultaneously heated from both its top and bottom surfaces. Similar to the microwave-based heating/drying arrangement described in FIG. 3, gravity (as shown by the white arrowhead) continues to drain the liquid pre-mixture downward toward the bottom region in such impingement oven-based heating/drying arrangement of FIG. 4. As a result, the solidified sheet so formed has more uniformly distributed and more evenly sized pores, in comparison with sheet formed by the convection-based heating/drying arrangement. However, the liquid drainage under gravity force during the drying step may still result in a dense bottom region with thick cell walls. Further, nearly simultaneous heating of the sheet 42 from both directions may still limit the pore expansion and pore opening on the top surface during the drying step, and the resulting sheet may still have a top surface with relatively smaller pore openings.

Figure 4:
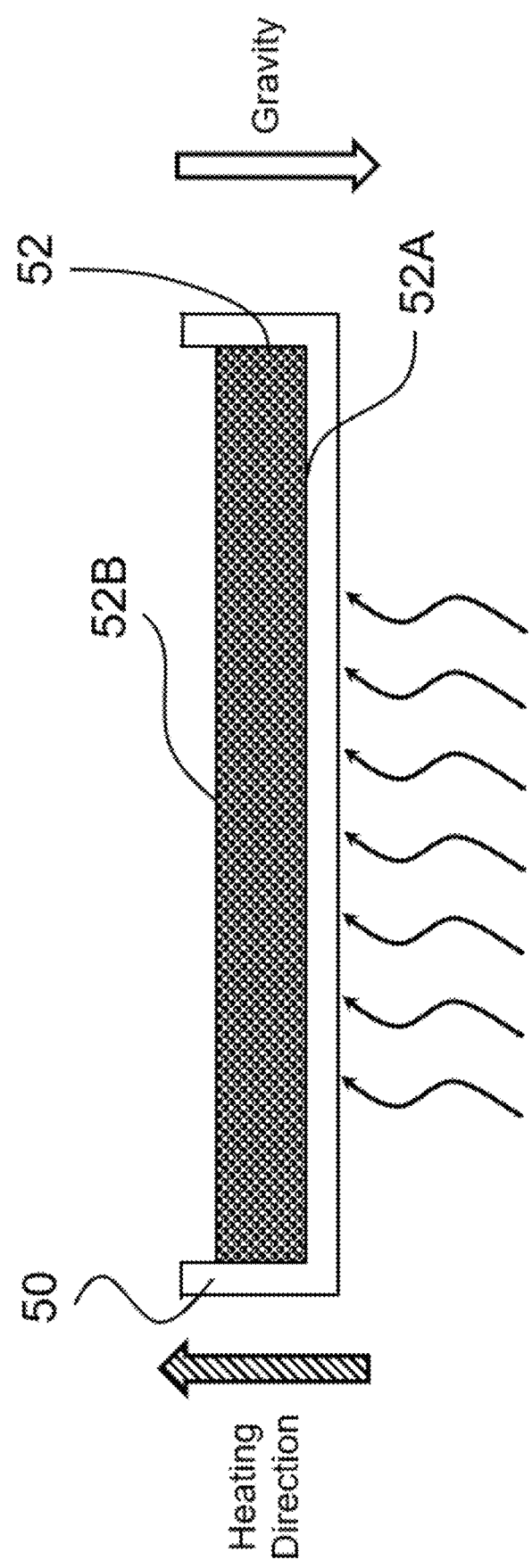
FIG. 4 shows a bottom conduction-based heating/drying arrangement for making an flexible, porous, dissolvable sheet in a batch process.

In contrast to the above-described heating/drying arrangements (convection-based, microwave-based or impingement oven-based), the present invention provides a heating/drying arrangement for drying the aerated wet pre-mixture, in which the direction of heating is purposefully configured to counteract/reduce liquid drainage caused by the gravitational force toward the bottom region (thereby reducing the density and improving pore structures in the bottom region) and to allow more time for the air bubbles near the top surface to expand during drying (thereby forming significantly larger pore openings on the top surface of the resulting sheet). Both features function to improve overall dissolution rate of the sheet and are therefore desirable. FIG. 4 shows a bottom conduction-based heating/drying arrangement for making a flexible, porous, dissolvable sheet, according to one example. Specifically, a mold 50 is filled with an aerated wet pre-mixture, which forms a sheet 52 having a first side 52A (i.e., the bottom side) and an opposing second side 52B (i.e., the top side). Such mold 50 is placed on a heated surface (not shown), for example, on top of a pre-heated Peltier plate with a controlled surface temperature of about 125-130° C., for approximately 30 minutes during the drying step. Heat is conducted from the heated surface at the bottom of the mold 50 through the mold to heat the sheet 52 from below, i.e., along an upward heating direction (as shown by the cross-hatched arrowhead), which forms a temperature gradient in the sheet 52 that decreases from the first side 52A (the bottom side) to the opposing second side 52B (the top side). Such an upward heating direction is opposite to the gravitational direction (as shown by the white arrowhead), and it is maintained as so throughout the entire drying time (i.e., the heating direction is opposite to the gravitational direction for almost 100% of the drying time). During drying, the gravitational force still drains the liquid pre-mixture downward toward the bottom region. However, the upward heating direction dries the sheet from bottom up, and water vapor generated by heat at the bottom region arises upward to escape from the solidifying matrix, so the downward liquid drainage toward the bottom region is significantly limited and "counteracted"/reduced by the solidifying matrix and the uprising water vapor. Correspondingly, the bottom region of the resulting dry sheet is less dense and contains numerous pores with relatively thin cell walls. Further, because the top region is the last region that is dried during this process, the air bubbles in the top region have sufficient time to expand to form significantly larger open pores at the top surface of the resulting sheet, which are particularly effective in facilitating water ingress into the sheet. Moreover, the resulting sheet has a more evenly distributed overall pore sizes throughout different regions (e.g., top, middle, bottom) thereof.

Figure 5:
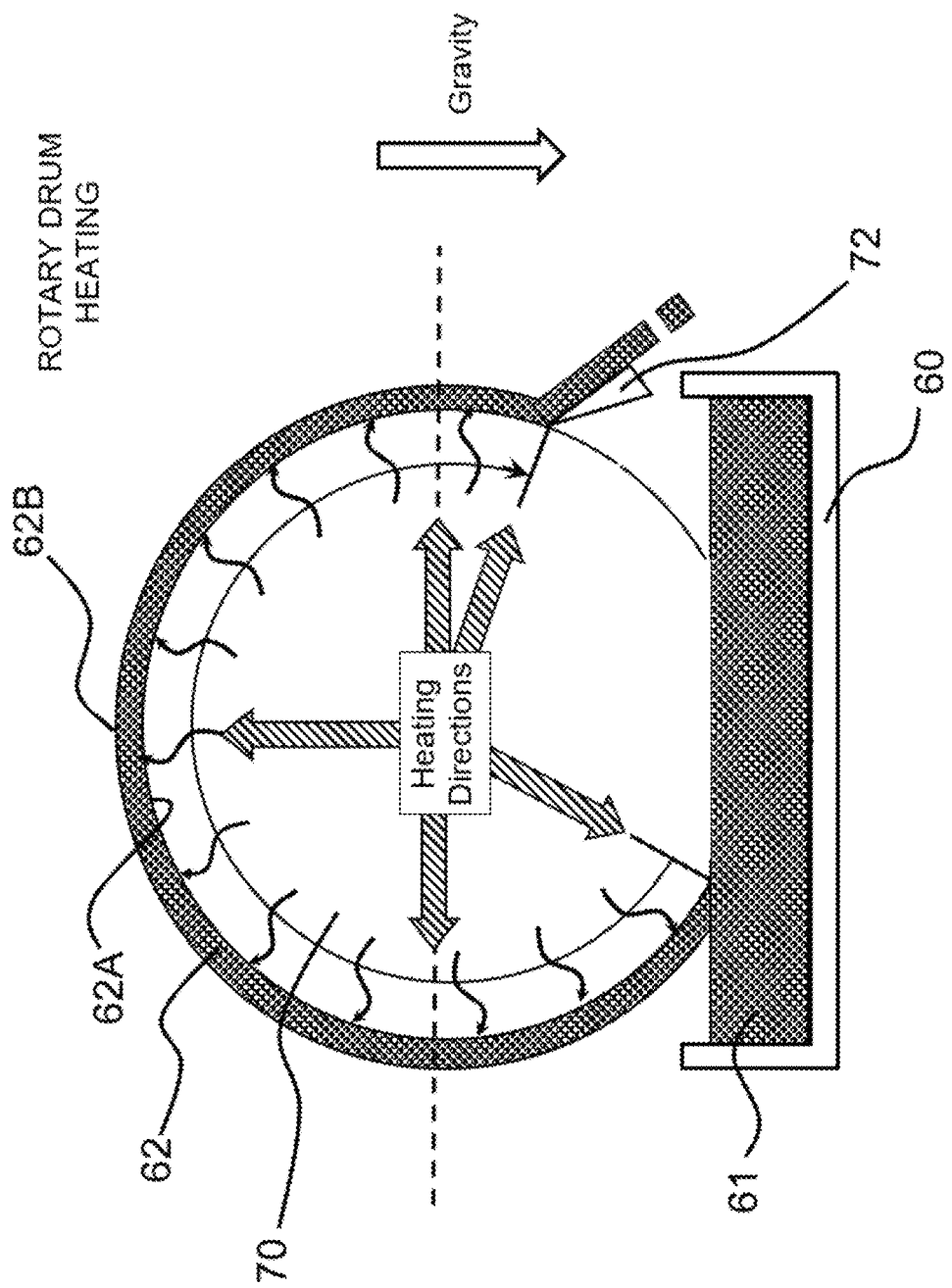
FIG. 5 shows a rotary drum-based heating/drying arrangement for making another flexible, porous, dissolvable sheet in a continuous process.

FIG. 5 shows a rotary drum-based heating/drying arrangement for making a flexible, porous, dissolvable sheet, according to another example. Specifically, a feeding trough 60 is filled with an aerated wet pre-mixture 61. A heated rotatable cylinder 70 (also referred to as a drum dryer) is placed above the feeding trough 60. The heated drum dryer 70 has a cylindrical heated outer surface characterized by a controlled surface temperature of about 130° C., and it rotates along a clock-wise direction (as shown by the thin curved line with an arrowhead) to pick up the aerated wet pre-mixture 61 from the feeding trough 60. The aerated wet pre-mixture 61 forms a thin sheet 62 over the cylindrical heated outer surface of the drum dryer 70, which rotates and dries such sheet 62 of aerated wet pre-mixture in approximately 10-15 minutes. A leveling blade (not shown) may be placed near the slurry pick-up location to ensure a consistent thickness of the sheet 62 so formed, although it is possible to control the thickness of sheet 62 simply by modulating the viscosity of the aerated wet pre-mixture 61 and the rotating speed and surface temperature of the drum dryer 70. Once dried, the sheet 62 can then picked up, either manually or by a scraper 72 at the end of the drum rotation.

As shown in FIG. 5, the sheet 62 formed by the aerated wet pre-mixture 61 comprises a first side 62A (i.e., the bottom side) that directly contacts the heated outer surface of the heated drum dryer 70 and an opposing second side 62B (i.e., the top side). Correspondingly, heat from the drum dryer 70 is conducted to the sheet 62 along an outward heating direction, to heat the first side 62A (the bottom side) of the sheet 62 first and then the opposing second side 62B (the top side). Such outward heating direction forms a temperature gradient in the sheet 62 that decreases from the first side 62A (the bottom side) to the opposing second side 62B (the top side). The outward heating direction is slowly and constantly changing as the drum dryer 70 rotates, but along a very clear and predictable path (as shown by the multiple outwardly extending cross-hatched arrowheads in FIG. 5). The relative position of the outward heating direction and the gravitational direction (as shown by the white arrowhead) is also slowing and constantly changing in a similar clear and predictable manner. For less than half of the drying time (i.e., when the heating direction is below the horizontal dashed line), the outward heating direction is substantially aligned with the gravitational direction with an offset angle of less than 90° in between. During majority of the drying time (i.e., when the heating direction is flushed with or above the horizontal dashed line), the outward heating direction is opposite or substantially opposite to the gravitational direction with an offset angle of 90° or more therebetween. Depending on the initial "start" coating position of the sheet 62, the heating direction can be opposite or substantially opposite to the gravitational direction for more than 55% of the drying time (if the coating starts at the very bottom of the drum dryer 70), more than 60% of the drying time (if the coating starts at a higher position of the drum dryer 70, as shown in FIG. 5). Consequently, during most of the drying step this slowing rotating and changing heating direction in the rotary drum-based heating/drying arrangement can still function to limit and "counteract"/reduce the liquid drainage in sheet 62 caused by the gravitational force, resulting in improved OCF structures in the sheet so formed. The resulting sheet as dried by the heated drum dryer 70 is also characterized by a less dense bottom region with numerous more evenly sized pores, and a top surface with relatively larger pore openings. Moreover, the resulting sheet has a more evenly distributed overall pore sizes throughout different regions (e.g., top, middle, bottom) thereof.

In addition to employing the desired heating direction (i.e., in a substantially offset relation with respect to the gravitational direction) as mentioned hereinabove, it may also be desirable and even important to carefully adjust the viscosity and/or solid content of the wet pre-mixture, the amount and speed of aeration (air feed pump speed, mixing head speed, air flow rate, density of the aerated pre-mixture and the like, which may affect bubble sizes and quantities in the aerated pre-mixture and correspondingly impact the pore size/distribution/quantity/characteristics in the solidified sheet), the drying temperature and the drying time, in order to achieve optimal OCF structure in the resulting sheet according to the present invention.

More detailed descriptions of the processes for making the flexible, porous, dissolvable sheets according to the present invention, as well as the physical and chemical characteristics of such sheets, are provided in the ensuring sections.

III. Process of Making Solid Sheets

The present invention provides a new and improved method for making flexible, porous, dissolvable solid sheets, which comprises the steps of: (a) forming a pre-mixture containing raw materials (e.g., the water-soluble polymer, active ingredients such as surfactants, and optionally a plasticizer) dissolved or dispersed in water or a suitable solvent, which is characterized by a viscosity of from about 1,000 cps to about 25,000 cps measured at about 40° C. and 1 s$^{-1}$; (b) aerating the pre-mixture (e.g., by introducing a gas into the wet slurry) to form an aerated wet pre-mixture; (c) forming the aerated wet pre-mixture into a sheet having opposing first and second sides; and (d) drying the formed sheet for a drying time of from 1 minute to 60 minutes at a temperature from 70° C. to 200° C. along a heating direction that forms a temperature gradient decreasing from the first side to the second side of the formed sheet, wherein the heating direction is substantially offset from the gravitational direction for more than half of the drying time, i.e., the drying step is conducted under heating along a mostly "anti-gravity" heating direction. Such a mostly "anti-gravity" heating direction can be achieved by various means, which include but are not limited to the bottom conduction-based heating/drying arrangement and the rotary drum-based heating/drying arrangement, as illustrated hereinabove in FIGS. 4 and 5 respectively.

Step (A): Preparation of Wet Pre-Mixture

The wet pre-mixture is generally prepared by mixing solids of interest, including the water-soluble polymer, surfactant(s) and/or other benefit agents, optional plasticizer, and other optional ingredients, with a sufficient amount of water or another solvent in a pre-mix tank. The wet pre-mixture can be formed using a mechanical mixer. Mechanical mixers useful herein, include, but aren't limited to pitched blade turbines or MAXBLEND mixer (Sumitomo Heavy Industries).

It is particularly important herein to adjust viscosity of the wet pre-mixture so that it is within a predetermined range of from about 1,000 cps to about 25,000 cps when measured at 40° C. and 1 s$^{-1}$. Viscosity of the wet pre-mixture may have a significant impact on the pore expansion and pore opening of the aerated pre-mixture during the subsequent drying step, and wet pre-mixtures with different viscosities may form flexible, porous, dissolvable solid sheets of very different foam structures. On one hand, when the wet pre-mixture is too thick/viscous (e.g., having a viscosity higher than about 25,000 cps as measured at 40° C. and 1 s$^{-1}$), aeration of such wet pre-mixture may become more difficult. More importantly, interstitial liquid drainage from thin film bubble facings into the plateau borders of the three-dimensional foam during the subsequent drying step may be adversely affected or significantly limited. The interstitial liquid drainage during drying is believed to be critical for enabling pore expansion and pore opening in the aerated wet pre-mixture during the subsequent drying step. As a result, the flexible, porous, dissolvable solid sheet so formed thereby may have significantly smaller pores and less interconnectivity between the pores (i.e., more "closed" pores than open pores), which render it harder for water to ingress into and egress from such sheet. On the other hand, when the wet pre-mixture is too thin/running (e.g., having a viscosity lower than about 1,000 cps as measured at 40° C. and 1 s$^{-1}$), the aerated wet pre-mixture may not be sufficiently stable, i.e., the air bubbles may rupture, collapse, or coalescence too quickly in the wet pre-mixture after aeration and before drying. Consequently, the resulting solid sheet may be much less porous and more dense than desired.

In one example, viscosity of the wet pre-mixture ranges from about 3,000 cps to about 24,000 cps, from about 5,000 cps to about 23,000 cps, or from about 10,000 cps to about 20,000 cps, as measured at 40° C. and 1 sec$^{-1}$. The pre-mixture viscosity values are measured using a Malvern Kinexus Lab+rheometer with cone and plate geometry (CP1/50 SR3468 SS), a gap width of 0.054 mm, a temperature of 40° C. and a shear rate of 1.0 reciprocal seconds for a period of 360 seconds.

Step (B): Aeration of Wet Pre-Mixture

Aeration of the wet pre-mixture is conducted in order to introduce a sufficient amount of air bubbles into the wet pre-mixture for subsequent formation of the OCF structures therein upon drying. Once sufficiently aerated, the wet pre-mixture is characterized by a density that is significantly lower than that of the non-aerated wet pre-mixture (which may contain a few inadvertently trapped air bubbles) or an insufficiently aerated wet pre-mixture (which may contain some bubbles but at a much lower volume percentage and of significantly larger bubble sizes). The aerated wet pre-mixture has a density ranging from about 0.05 g/ml to about 0.8 g/ml, from about 0.1 g/ml to about 0.75 g/ml, from about 0.15 g/ml to about 0.7 g/ml, from about 0.2 g/ml to about 0.6 g/ml, or from about 0.25 g/ml to about 0.5 g/ml.

Aeration can be accomplished by either physical or chemical means herein. In one example, it can be accomplished by introducing a gas into the wet pre-mixture through mechanical agitation, for example, by using any suitable mechanical processing means, including but not limited to: a rotor stator mixer, a planetary mixer, a pressurized mixer, a non-pressurized mixer, a batch mixer, a continuous mixer, a semi-continuous mixer, a high shear mixer, a low shear mixer, a submerged sparger, or any combinations thereof. In another example, it may be achieved via chemical means, for example, by using chemical foaming agents to provide in-situ gas formation via chemical reaction of one or more ingredients, including formation of carbon dioxide ($CO_2$ gas) by an effervescent system.

It has been discovered that the aeration of the wet pre-mixture can be cost-effectively achieved by using a continuous pressurized aerator or mixer that is conventionally utilized in the foods industry in the production of marshmallows. Continuous pressurized mixers may work to homogenize or aerate the wet pre-mixture to produce highly uniform and stable foam structures with uniform bubble sizes. The unique design of the high shear rotor/stator mixing head may lead to uniform bubble sizes in the layers of the open celled foam. Suitable continuous pressurized aerators or mixers include the Morton whisk (Morton Machine Co., Motherwell, Scotland), the Oakes continuous automatic mixer (E.T. Oakes Corporation, Hauppauge, New York), the Fedco Continuous Mixer (The Peerless Group, Sidney, Ohio), the Mondo (Haas-Mondomix B.V., Netherlands), the Aeros (Aeros Industrial Equipment Co., Ltd., Guangdong Province, China), and the Preswhip (Hosokawa Micron Group, Osaka, Japan). For example, an Aeros A20 continuous aerator can be operated at a feed pump speed setting of about 300-800 (or at about 500-700) with a mixing head speed setting of about 300-800 (or about 400-600) and an air flow rate of about 50-150 (60-130, or 80-120) respectively. For another example, an Oakes continuous automatic mixer can be operated at a mixing head speed setting of about 10-30 rpm (about 15-25 rpm, or about 20 rpm) with an air flow rate of about 10-30 Litres per hour (about 15-25 L/hour, or about 19-20 L/hour).

In another specific example, aeration of the wet pre-mixture can be achieved by using the spinning bar that is a part of the rotary drum dryer, more specifically a component of the feeding trough where the wet pre-mixture is stored before it is coated onto the heated outer surface of the drum dryer and dried. The spinning bar is typically used for stirring the wet pre-mixture to preventing phase separation or sedimentation in the feeding trough during the waiting time before it is coated onto the heated rotary drum of the drum dryer. It is possible to operate such spinning bar at a rotating speed ranging from about 150 to about 500 rpm, from about 200 to about 400 rpm, or from about 250 to about 350 rpm, to mix the wet pre-mixture at the air interface and provide sufficient mechanical agitation needed for achieving the desired aeration of the wet pre-mixture.

As mentioned hereinabove, the wet pre-mixture can be maintained at an elevated temperature during the aeration process, so as to adjust viscosity of the wet pre-mixture for optimized aeration and controlled draining during drying. For example, when aeration is achieved by using the spinning bar of the rotary drum, the aerated wet pre-mixture in the feeding trough is typically maintained at about 60° C. during initial aeration by the spinning bar (while the rotary drum is stationary), and then heated to about 70° C. when the rotary drum is heated up and starts rotating.

Bubble size of the aerated wet pre-mixture assists in achieving uniform layers in the OCF structures of the resulting solid sheet. In one example, the bubble size of the aerated wet pre-mixture is from about 5 to about 100 microns; and in another example, the bubble size is from about 20 microns to about 80 microns. Uniformity of the bubble sizes causes the resulting solid sheets to have consistent densities.

Step (C): Sheet-Forming

After sufficient aeration, the aerated wet pre-mixture forms one or more sheets with opposing first and second sides. The sheet-forming step can be conducted in any suitable manners, e.g., by extrusion, casting, molding, vacuum-forming, pressing, printing, coating, and the like. More specifically, the aerated wet pre-mixture can be formed into a sheet by: (i) casting it into shallow cavities or trays or specially designed sheet moulds; (ii) extruding it onto a continuous belt or screen of a dryer, (iii) coating it onto the outer surface of a rotary drum dryer. The supporting surface upon which the sheet is formed can be made from or coated with materials that are anti-corrosion, non-interacting and/or non-sticking, such as metal (e.g., steel, chromium, and the like), TEFLON®, polycarbonate, NEOPRENE®, HDPE, LDPE, rubber, glass and the like.

The formed sheet of aerated wet pre-mixture can have a thickness ranging from 0.5 mm to 4 mm, from 0.6 mm to 3.5 mm, from 0.7 mm to 3 mm, from 0.8 mm to 2 mm, or from 0.9 mm to 1.5 mm. Controlling the thickness of such formed sheet of aerated wet pre-mixture may be important for ensuring that the resulting solid sheet has the desired OCF structures. If the formed sheet is too thin (e.g., less than 0.5 mm in thickness), many of the air bubbles trapped in the aerated wet pre-mixture will expand during the subsequent drying step to form through-holes that extend through the entire thickness of the resulting solid sheet. Such through-holes, if too many, may significantly compromise both the overall structural integrity and aesthetic appearance of the sheet. If the formed sheet is too thick, not only it will take longer to dry, but also it will result in a solid sheet with greater pore size variations between different regions (e.g., top, middle, and bottom regions) along its thickness, because the longer the drying time, the more imbalance of forces may occur through bubble rupture/collapse/coalescence, liquid drainage, pore expansion, pore opening, water evaporation, and the like. Further, multiple layers of relatively thin sheets can be assembled into three-dimensional structures of greater thickness to deliver the desired cleaning benefits or other benefits, while still providing satisfactory pore structures for fast dissolution as well as ensuring efficient drying within a relatively short drying time.

Step (D): Drying Under Anti-Gravity Heating

A key feature of the herein is the use of an anti-gravity heating direction during the drying step, either through the entire drying time or at least through more than half of the drying time. Without being bound by any theory, it is believed that such anti-gravity heating direction may reduce or counteract excessive interstitial liquid drainage toward the bottom region of the formed sheet during the drying step. Further, because the top surface is dried last, it allows longer time for air bubbles near the top surface of the formed sheet to expand and form pore openings on the top surface (because once the wet matrix is dried, the air bubbles can no longer expand or form surface openings). Consequently, the solid sheet formed by drying with such anti-gravity heating is characterized by improved OCF structures that enables faster dissolution as well as other surprising and unexpected benefits.

In a specific example, the anti-gravity heating direction is provided by a conduction-based heating/drying arrangement, either the same or similar to that illustrated by FIG. 4. For example, the aerated wet pre-mixture can be casted into a mold to form a sheet with two opposing sides. The mold can then be placed on a hot plate or a heated moving belt or any other suitable heating device with a planar heated surface characterized by a controlled surface temperature of from about 80° C. to about 170° C., from about 90° C. to about 150° C., or from about 100° C. to about 140° C. Thermal energy is transferred from the planar heated surface to the bottom surface of the sheet of aerated wet pre-mixture via conduction, so that solidification of the sheet starts with the bottom region and gradually moves upward to reach the top region last. In order to ensure that the heating direction is primarily anti-gravity (i.e., substantially offset from the gravitational direction) during this process, the heated surface can be a primary heat source for the sheet during drying. If there are any other heating sources, the overall heating direction may change accordingly. The heated surface may be the only heat source for the sheet during drying.

In another specific example, the anti-gravity heating direction is provided by a rotary drum-based heating/drying arrangement, which is also referred to as drum drying or roller drying, similar to that illustrated in FIG. 5. Drum drying is one type of contact-drying methods, which is used for drying out liquids from a viscous pre-mixture of raw materials over the outer surface of a heated rotatable drum (also referred to as a roller or cylinder) at relatively low temperatures to form sheet-like articles. It is a continuous drying process particularly suitable for drying large volumes. Because the drying is conducted at relatively low temperatures via contact-heating/drying, it normally has high energy efficiency and does not adversely affect the compositional integrity of the raw materials.

The heated rotatable cylinder used in drum drying is heated internally, e.g., by steam or electricity, and it is rotated by a motorized drive installed on a base bracket at a predetermined rotational speed. The heated rotatable cylinder or drum can have an outer diameter ranging from about 0.5 meters to about 10 meters, from about 1 meter to about 5 meters, or from about 1.5 meters to about 2 meters. It may have a controlled surface temperature of from about 80° C. to about 170° C., from about 90° C. to about 150° C., or from about 100° C. to about 140° C. Further, such heated rotatable cylinder is rotating at a speed of from about 0.005 rpm to about 0.25 rpm, from about 0.05 rpm to about 0.2 rpm, or from about 0.1 rpm to about 0.18 rpm.

The total drying time depends on the formulations and solid contents in the wet pre-mixture, the drying temperature, the thermal energy influx, and the thickness of the sheet material to be dried. The drying time may be from about 1 minute to about 60 minutes, from about 2 minutes to about 30 minutes, from about 2 to about 15 minutes, from about 2 to about 10 minutes, or from about 2 to about 5 minutes.

During such drying time, the heating direction is so arranged that it is substantially opposite to the gravitational direction for more than half of the drying time, for more than 55% or 60% of the drying time (e.g., as in the rotary drum-based heating/drying arrangement described hereinabove), or for more than 75% or even 100% of the drying time (e.g., as in the bottom conduction-based heating/drying arrangement described hereinabove). Further, the sheet of aerated wet pre-mixture can be dried under a first heating direction for a first duration and then under a second, opposite heating direction under a second duration, while the first heating direction is substantially opposite to the gravitational direction, and while the first duration is anywhere from 51% to 99% (e.g., from 55%, 60%, 65%, 70% to 80%, 85%, 90% or 95%) of the total drying time.

Such change in heating direction can be readily achieved by various other arrangements not illustrated herein, e.g., by an elongated heated belt of a serpentine shape that can rotate along a longitudinal central axis.

IV. Physical Characteristics of Solid Sheets

The flexible, porous, dissolvable solid sheet formed by the above-described processing steps is characterized by improved pore structures that allows easier water ingress into the sheet and faster dissolution of the sheet in water. Such improved pore structures are achieved mainly by adjusting various processing conditions as described hereinabove, and they are relatively independent or less influenced by the chemical formulations or the specific ingredients used for making such sheet. The sheet and/or article may have a Young's modulus of no more than 5 GPa, no more than 1 GPa, no more than 0.5 GPa, or no more than 0.2 GPa. The sheet and/or article may completely dissolve in or disperse into water leaving no visible solids or forming no visibly separate phase, when at least about 25 grams, at least about 50 grams, at least about 100 grams, or at least about 200 grams, of such material is placed in one liter (1 L) of deionized water at 20° C. and under the atmospheric pressure with sufficient stirring.

In general, such solid sheet may be characterized by: (i) a Percent Open Cell Content of from about 80% to 100%, from about 85% to 100%, or from about 90% to 100%, as measured by the Test 3 hereinafter; and (ii) an Overall Average Pore Size of from about 100 μm to about 2000 μm, from about 150 μm to about 1000 μm, or from about 200 μm to about 600 μm, as measured by the Micro-CT method described in Test 2 hereinafter. The Overall Average Pore Size defines the porosity of the OCF structure. The Percent Open Cell Content defines the interconnectivity between pores in the OCF structure. Interconnectivity of the OCF structure may also be described by a Star Volume or a Structure Model Index (SMI) as disclosed in WO2010077627 and WO2012138820.

Such solid sheet has opposing top and bottom surfaces, while its top surface may be characterized by a Surface Average Pore Diameter that is greater than about 100 μm, greater than about 110 μm, greater than about 120 μm, greater than about 130 μm, or greater than about 150 μm, as measured by the SEM method described in Test 1 hereinafter. When comparing with solid sheets formed by conventional heating/drying arrangements (e.g., the convection-based, the microwave-based, or the impingement oven-based arrangements), the solid sheet formed by the improved heating/drying arrangement has a significantly larger Surface Average Pore Diameter at its top surface (as demonstrated by FIGS. 6A-6B, which are described in detail in Example 1 hereinafter), because under the specifically arranged directional heating, the top surface of the formed sheet of aerated wet pre-mixture is the last to dry/solidify, and the air bubbles near the top surface has the longest time to expand and form larger pore openings at the top surface.

Still further, the solid sheet formed by the improved heating/drying (for example, rotary drum-based heating/ drying) arrangement is characterized by a more uniform pore size distribution between different regions along its thickness direction, in comparison with the sheets formed by other heating/drying arrangements (for example, impingement oven-based). Specifically, the solid sheet comprises a top region adjacent to the top surface, a bottom region adjacent to the bottom surface, and a middle region therebetween, while the top, middle, and bottom regions all have the same thickness. Each of the top, middle and bottom regions of such solid sheet is characterized by an Average Pore Size, while the ratio of Average Pore Size in the bottom region over that in the top region (i.e., bottom-to-top Average Pore Size ratio) is from about 0.6 to about 1.5, from about 0.7 to about 1.4, from about 0.8 to about 1.3, or from about 1 to about 1.2. In comparison, a solid sheet formed by an impingement oven-based heating/drying arrangement may have a bottom-to-top Average Pore Size ratio of more than 1.5, typically about 1.7-2.2 (as demonstrated in Example 1 hereinafter). Moreover, the solid sheet may be characterized by a bottom-to-middle Average Pore Size ratio of from about 0.5 to about 1.5, from about 0.6 to about 1.3, from about 0.8 to about 1.2, or from about 0.9 to about 1.1, and a middle-to-top Average Pore Size ratio of from about 1 to about 1.5, from about 1 to about 1.4, or from about 1 to about 1.2.

Still further, the relative standard deviation (RSTD) between Average Pore Sizes in the top, middle and bottom regions of the solid sheet is no more than 20%, no more than 15%, no more than 10%, no more than 5%. In contrast, a solid sheet formed by an impingement oven-based heating/drying arrangement may have a relative standard deviation (RSTD) between top/middle/bottom Average Pore Sizes of more than 20%, likely more than 25% or even more than 35% (as demonstrated in Example 1 hereinafter).

The solid sheet may be further characterized by an Average Cell Wall Thickness of from about 5 μm to about 200 μm, from about 10 μm to about 100 μm, or from about 10 μm to about 80 μm, as measured by Test 2 hereinafter.

The solid sheet may contain a small amount of water. It may be characterized by a final moisture content of from 0.5% to 25%, from 1% to 20%, or from 3% to 10%, by weight of the solid sheet, as measured by Test 4 hereinafter. An appropriate final moisture content in the resulting solid sheet may ensure the desired flexibility/deformability of the sheet, as well as providing soft/smooth sensory feel to the consumers. If the final moisture content is too low, the sheet may be too brittle or rigid. If the final moisture content is too high, the sheet may be too sticky, and its overall structural integrity may be compromised.

The solid sheet may have a thickness ranging from about 0.6 mm to about 3.5 mm, from about 0.7 mm to about 3 mm, from about 0.8 mm to about 2 mm, or from about 1 mm to about 2 mm. Thickness of the solid sheet can be measured using Test 6 described hereinafter. The solid sheet after drying may be slightly thicker than the sheet of aerated wet pre-mixture, due to pore expansion that in turn leads to overall volume expansion.

The solid sheet may further be characterized by a basis weight of from about 50 grams/m² to about 500 grams/m², from about 150 grams/m² to about 450 grams/m², or from about 250 grams/m² to about 400 grams/m², as measured by Test 6 described hereinafter.

Still further, the solid sheet may have a density ranging from about 0.05 grams/cm³ to about 0.5 grams/cm³, from about 0.06 grams/cm³ to about 0.4 grams/cm³, from about 0.07 grams/cm³ to about 0.2 grams/cm³, or from about 0.08 grams/cm³ to about 0.15 grams/cm³, as measured by Test 7 hereinafter. Density of the solid sheet is lower than that of the sheet of aerated wet pre-mixture, also due to pore expansion that in turn leads to overall volume expansion.

In some examples, the solid sheets may have a density of from about 0.06 grams/cm³ to about 0.16 grams/cm³, from about 0.07 grams/cm³ to about 0.15 grams/cm³, or from about 0.08 grams/cm³ to about 0.145 grams/cm³. The solid article containing sheets with such relatively low density may achieve even more improved leakage performance.

Furthermore, the solid sheet can be characterized by a Specific Surface Area of from about 0.03 m²/g to about 0.25 m²/g, from about 0.04 m²/g to about 0.22 m²/g, from 0.05 m²/g to 0.2 m²/g, from 0.1 m²/g to 0.18 m²/g, as measured by Test 8 described hereinafter. The Specific Surface Area of the solid sheet may be indicative of its porosity and may impact its dissolution rate, e.g., the greater the Specific Surface Area, the more porous the sheet and the faster its dissolution rate.

The solid sheet and/or the dissolvable solid article may be characterized by:
- a Percent Open Cell Content of from 85% to 100%, from 90% h to 100%; and/or
- an Overall Average Pore Size of from 150 μm to 1000 μm, from 200 μm to 600 μm; and/or
- an Average Cell Wall Thickness of from 5 μm to 200 μm, from 10 μm to 100 μm, from 10 μm to 80 μm; and/or
- a final moisture content of from 0.5% to 25%, from 1% to 20%, from 3% to 10%, by weight of the solid sheet article; and/or
- a thickness of from 0.6 mm to 3.5 mm, from 0.7 mm to 3 mm, from 0.8 mm to 2 mm, from 1 mm to 2 mm; and/or
- a basis weight of from about 50 grams/m² to about 500 grams/m², from about 150 grams/m² to about 450 grams/m², from about 250 grams/m² to about 400 grams/m²; and/or
- a density of from 0.05 grams/cm³ to 0.5 grams/cm³, from 0.06 grams/cm³ to 0.4 grams/cm³, from 0.07 grams/cm³ to 0.2 grams/cm³, from 0.08 grams/cm³ to 0.15 grams/cm³; and/or
- a Specific Surface Area of from about 0.03 m²/g to 0.25 m²/g, from 0.04 m²/g to 0.22 m²/g, from 0.05 m²/g to 0.2 m²/g, from 0.1 m²/g to 0.18 m²/g.

V. Formulations of Solid Sheets

1. Water-Soluble Polymer

As mentioned hereinabove, the flexible, porous, dissolvable solid sheet may be formed by a wet pre-mixture that comprises a water-soluble polymer and a first surfactant. Such a water-soluble polymer may function in the resulting solid sheet as a film-former, a structurant as well as a carrier for other active ingredients (e.g., surfactants, emulsifiers, builders, chelants, perfumes, colorants, and the like).

The wet pre-mixture may comprise from about 3% to about 20% by weight of the pre-mixture of water-soluble polymer, in one example from about 5% to about 15% by weight of the pre-mixture of water-soluble polymer, in one example from about 7% to about 10% by weight of the pre-mixture of water-soluble polymer.

After drying, it the water-soluble polymer may be present in the flexible, porous, dissolvable solid sheet in an amount ranging from about 5% to about 60%, from about 7% to about 50%, from about 9% to about 40%, from about 10% to about 30%, for example 10%, 12%, 15%, 18%, 20%, 25%, 30% or any ranges therebetween, by total weight of the solid sheet. The total amount of water-soluble polymer(s) present in the flexible, porous, dissolvable solid sheet may be no more than 25% by total weight of such sheet.

Water-soluble polymers suitable for use herein may be selected those with weight average molecular weights ranging from about 5,000 to about 400,000 Daltons, from about 10,000 to about 300,000 Daltons, from about 15,000 to about 200,000 Daltons, from about 20,000 to about 150,000 Daltons. The weight average molecular weight is computed by summing the average molecular weights of each polymer raw material multiplied by their respective relative weight percentages by weight of the total weight of polymers present within the porous solid sheet. The weight average molecular weight of the water-soluble polymer used herein may impact the viscosity of the wet pre-mixture, which may in turn influence the bubble number and size during the aeration step as well as the pore expansion/opening results during the drying step. Further, the weight average molecular weight of the water-soluble polymer may affect the overall film-forming properties of the wet pre-mixture and its compatibility/incompatibility with certain surfactants.

The water-soluble polymers may include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, copolymers of acrylic acid and methyl acrylate, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymers may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers can also be used as water-soluble polymers herein. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

The water-soluble polymer may include starch. As used herein, the term "starch" includes both naturally occurring or modified starches. Typical natural sources for starches can include cereals, tubers, roots, legumes and fruits. More specific natural sources can include corn, pea, potato, banana, barley, wheat, rice, sago, amaranth, tapioca, arrowroot, canna, sorghum, and waxy or high amylase varieties thereof. The natural starches can be modified by any modification method known in the art to form modified starches, including physically modified starches, such as sheared starches or thermally-inhibited starches; chemically modified starches, such as those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof; conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

Water-soluble polymers may include polyvinyl alcohols, polyvinylpyrrolidones, polyalkylene oxides, starch and starch derivatives, pullulan, gelatin, hydroxypropylmethylcelluloses, methycelluloses, and carboxymethycelluloses. In one example, the water-soluble polymers include polyvinyl alcohols, and/or hydroxypropylmethylcelluloses.

Polyvinyl alcohols may be characterized by a degree of hydrolysis ranging from about 40% to about 100%, from about 50% to about 95%, from about 65% to about 92%, or from about 70% to about 90% h. Commercially available polyvinyl alcohols include those from Celanese Corporation (Texas, USA) under the CELVOL trade name including, but not limited to, CELVOL 523, CELVOL 530, CELVOL 540, CELVOL 518, CELVOL 513, CELVOL 508, CELVOL 504; those from Kuraray Europe GmbH (Frankfurt, Germany) under the Mowiol® and POVAL™ trade names; and PVA 1788 (also referred to as PVA BP17) commercially available from various suppliers including Lubon Vinylon Co. (Nanjing, China); and combinations thereof. The flexible, porous, dissolvable solid sheet may comprise from about 10% to about 25%, or from about 15% to about 23%, by total weight of such sheet, of a polyvinyl alcohol having a weight average molecular weight ranging from 80,000 to about 150,000 Daltons and a degree of hydrolysis ranging from about 80% to about 90%.

In addition to polyvinyl alcohols as mentioned hereinabove, a single starch or a combination of starches may be used as a filler material in such an amount as to reduce the overall level of water-soluble polymers required, so long as it helps provide the solid sheet with the requisite structure and physical/chemical characteristics as described herein. However, too much starch may comprise the solubility and structural integrity of the sheet. Therefore, it is desired that the solid sheet comprises no more than 20%, from 0% to 10%, from 0% to 5%, from 0% to 1%, by weight of the solid sheet, of starch.

2. Surfactants

In addition to the water-soluble polymer described hereinabove, the solid sheet comprises a surfactant. The surfactant may function as emulsifying agents during the aeration process to create a sufficient amount of stable bubbles for forming the desired OCF structure. Further, the surfactant may function as active ingredients for delivering a desired cleansing benefit.

The solid sheet may comprise a surfactant selected from the group consisting of anionic surfactants, nonionic surfactants, cationic surfactants, zwitterionic surfactants, amphoteric surfactants, polymeric surfactants and any combinations thereof. Depending on the desired application of such solid sheet and the desired consumer benefit to be achieved, different surfactants can be selected. One benefit is that the OCF structures of the solid sheet allow for incorporation of a high surfactant content while still providing fast dissolution. Consequently, highly concentrated cleansing compositions can be formulated into the solid sheets to provide a new and superior cleansing experience to the consumers.

The surfactant as used herein may include both surfactants from the conventional sense (i.e., those providing a consumer-noticeable lathering effect) and emulsifiers (i.e., those that do not provide any lathering performance but are intended primarily as a process aid in making a stable foam structure). Examples of emulsifiers for use as a surfactant component herein include mono- and di-glycerides, fatty alcohols, polyglycerol esters, propylene glycol esters, sorbitan esters and other emulsifiers known or otherwise commonly used to stabilize air interfaces.

The total amount of the surfactant present in the solid sheet may range widely from about 5% to about 95%, from about 30% to about 90%, from about 40/to about 80%, from about 50% to about 70%, e.g. 20%, 30%, 40%, 50%, 60%, 70%, 80% or any ranges therebetween, by total weight of the solid sheet. Correspondingly, the wet pre-mixture may comprise from about 1% to about 50% by weight of the wet pre-mixture of surfactant(s), in one example from about 2% to about 40% by weight of the wet pre-mixture of surfactant(s), in one example from about 10% to about 35% by weight of the wet pre-mixture of surfactant(s), in one example from about 15% to about 30% by weight of the wet pre-mixture of surfactant(s).

Non-limiting examples of anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

One category of anionic surfactants particularly suitable for practice herein include $C_6$-$C_{20}$ linear alkylbenzene sulphonate (LAS) surfactant. LAS surfactants are well known in the art and can be readily obtained by sulfonating commercially available linear alkylbenzenes. Exemplary $C_{10}$-$C_{20}$ linear alkylbenzene sulfonates that can be used herein include alkali metal, alkaline earth metal or ammonium salts of $C_{10}$-$C_{20}$ linear alkylbenzene sulfonic acids, and the sodium, potassium, magnesium and/or ammonium salts of $C_{11}$-$C_{18}$ or $C_{11}$-$C_{14}$ linear alkylbenzene sulfonic acids. It may be the sodium or potassium salts of $C_{12}$ and/or $C_{14}$ linear alkylbenzene sulfonic acids, i.e., sodium dodecylbenzene sulfonate and/or sodium tetradecylbenzene sulfonate.

LAS provides superior cleaning benefit and is especially suitable for use in laundry detergent applications. It has been a surprising and unexpected discovery herein that when polyvinyl alcohol having a higher weight average molecular weight (e.g., from about 50,000 to about 400,000 Daltons, from about 60,000 to about 300,000 Daltons, from about 70,000 to about 200,000 Daltons, from about 80,000 to about 150,000 Daltons) is used as the film-former and carrier, LAS can be used as a major surfactant, i.e., present in an amount that is more than 50% by weight of the total surfactant content in the solid sheet, without adversely affecting the film-forming performance and stability of the overall composition. Correspondingly, in a particular example, LAS is used as the major surfactant in the solid sheet. If present, the amount of LAS in the solid sheet may range from about 10% to about 70%, from about 20% to about 65%, from about 40% to about 60%, by total weight of the solid sheet.

Another category of anionic surfactants suitable for practice herein include sodium trideceth sulfates (STS) having a weight average degree of alkoxylation ranging from about 0.5 to about 5, from about 0.8 to about 4, from about 1 to about 3, from about 1.5 to about 2.5. Trideceth is a 13-carbon branched alkoxylated hydrocarbon comprising, in one example, an average of at least 1 methyl branch per molecule. STS used by the present invention may be include ST(EOxPOy)S, while EOx refers to repeating ethylene oxide units with a repeating number x ranging from 0 to 5, from 1 to 4, from 1 to 3, and while POy refers to repeating propylene oxide units with a repeating number y ranging from 0 to 5, from 0 to 4, from 0 to 2. It is understood that a material such as ST2S with a weight average degree of ethoxylation of about 2, for example, may comprise a significant amount of molecules which have no ethoxylate, 1 mole ethoxylate, 3 mole ethoxylate, and so on, while the distribution of ethoxylation can be broad, narrow or truncated, which still results in an overall weight average degree of ethoxylation of about 2. STS is particularly suitable for personal cleansing applications, and it has been a surprising and unexpected discovery herein that when polyvinyl alcohol having a higher weight average molecular weight (e.g., from about 50,000 to about 400,000 Daltons, from about 60,000 to about 300,000 Daltons, from about 70,000 to about 200,000 Daltons, from about 80,000 to about 150,000 Daltons) is used as the film-former and carrier, STS can be used as a major surfactant, i.e., present in an amount that is more than 50% by weight of the total surfactant content in the solid sheet, without adversely affecting the film-forming performance and stability of the overall composition. Correspondingly, in a particular example herein, STS is used as the major surfactant in the solid sheet. If present, the amount of STS in the solid sheet may range from about 10% to about 70%, from about 20% to about 65%, from about 40% to about 60%, by total weight of the solid sheet.

Another category of anionic surfactants suitable for practice include alkyl sulfates. These materials have the respective formulae $ROSO_3M$, wherein R is alkyl or alkenyl of from about 6 to about 20 carbon atoms, x is 1 to 10, and M is a water-soluble cation such as ammonium, sodium, potassium and triethanolamine. R may have from about 6 to about 18, from about 8 to about 16, from about 10 to about 14, carbon atoms. Previously, unalkoxylated $C_6$-$C_{20}$ linear or branched alkyl sulfates (AS) have been considered the preferred surfactants in dissolvable solid sheets, especially as the major surfactant therein, due to its compatibility with low molecular weight polyvinyl alcohols (e.g., those with a weight average molecular weight of no more than 50,000 Daltons) in film-forming performance and storage stability. However, it has been a surprising and unexpected discovery that when polyvinyl alcohol having a higher weight average molecular weight (e.g., from about 50,000 to about 400,000 Daltons, from about 60,000 to about 300,000 Daltons, from about 70,000 to about 200,000 Daltons, from about 80,000 to about 150,000 Daltons) is used as the film-former and carrier, other surfactants, such as LAS and/or STS, can be used as the major surfactant in the solid sheet, without adversely affecting the film-forming performance and stability of the overall composition. Therefore, it is desirable to provide a solid sheet with no more than about 20%/a, from 0% to about 10%, from 0% to about 5%, from 0% to about 1%, by weight of the solid sheet, of AS.

Another category of anionic surfactants include $C_6$-$C_{20}$ linear or branched alkylalkoxy sulfates (AAS). Among this category, linear or branched alkylethoxy sulfates (AES) having the respective formulae $RO(C_2H_4O)_xSO_3M$ can be utilized, wherein R is alkyl or alkenyl of from about 6 to about 20 carbon atoms, x is 1 to 10, and M is a water-soluble cation such as ammonium, sodium, potassium and triethanolamine. R may have from about 6 to about 18, from about 8 to about 16, from about 10 to about 14, carbon atoms.

Nonionic surfactants that can be included into the solid sheet may be any conventional nonionic surfactants, including but not limited to: alkyl alkoxylated alcohols, alkyl alkoxylated phenols, alkyl polysaccharides (especially alkyl glucosides and alkyl polyglucosides), polyhydroxy fatty acid amides, alkoxylated fatty acid esters, sucrose esters, sorbitan esters and alkoxylated derivatives of sorbitan esters, amine oxides, and the like. Nonionic surfactants can include those of the formula $R^1(OC_2H_4)_nOH$, wherein $R^1$ is a $C_8$-$C_{18}$ alkyl group or alkyl phenyl group, and n is from about 1 to about 80. For example, $C_8$-$C_{18}$, alkyl ethoxylated alcohols having a weight average degree of ethoxylation from about 1 to about 20, from about 5 to about 15, from about 7 to about 10, such as NEODOL® nonionic surfactants commercially available from Shell can be used. Other non-limiting examples of nonionic surfactants useful herein include: $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols (BA); $C_{14}$-$C_{22}$ mid-chain branched alkyl alkoxylates, $BAE_x$, wherein x is from 1 to 30; alkyl polysaccharides, specifically alkyl polyglycosides; Polyhydroxy fatty acid amides; and ether capped poly(oxyalkylated) alcohol surfactants. Suitable nonionic surfactants also include those sold under the tradename Lutensol® from BASF.

One example of a nonionic is a $C_6$-$C_2$a linear or branched alkylalkoxylated alcohols (AA) having a weight average degree of alkoxylation ranging from 5 to 15, $C_{12}$-$C_{14}$ linear ethoxylated alcohols having a weight average degree of alkoxylation ranging from 7 to 9. If present, the amount of AA-type nonionic surfactant(s) in the solid sheet may range from about 2% to about 40%, from about 5% to about 30%, or from about 8% to about 12%, by total weight of the solid sheet.

Amphoteric surfactants suitable for use in the solid sheet includes those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate, and N-higher alkyl aspartic acids.

Zwitterionic surfactants suitable include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

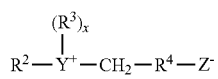

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Cationic surfactants can also be utilized herein, especially in fabric softener and hair conditioner products. When used in making products that contain cationic surfactants as the major surfactants, such cationic surfactants may be present in an amount ranging from about 2% to about 30%, from about 3% to about 20%, or from about 5% to about 15% by total weight of the solid sheet.

Cationic surfactants may include DEQA compounds, which encompass a description of diamido actives as well as actives with mixed amido and ester linkages. DEQA compounds are typically made by reacting alkanolamines such as MDEA (methyldiethanolamine) and TEA (triethanolamine) with fatty acids. Some materials that typically result from such reactions include N,N-di(acyl-oxyethyl)-N, N-dimethylammonium chloride or N,N-di(acyl-oxyethyl)-N,N-methylhydroxyethylammonium methylsulfate wherein the acyl group is derived from animal fats, unsaturated, and polyunsaturated, fatty acids.

Suitable polymeric surfactants for use in the personal care compositions include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

The surfactant may be selected from the group consisting of a $C_6$-$C_{20}$ linear alkylbenzene sulfonate (LAS), a $C_6$-$C_{20}$ linear or branched alkylalkoxy sulfates (AAS) having a weight average degree of alkoxylation ranging from 0.5 to 10, a $C_6$-$C_{20}$ linear or branched alkylalkoxylated alcohols (AA) having a weight average degree of alkoxylation ranging from 5 to 15, a $C_6$-$C_{20}$ linear or branched alkyl sulfates (AS) and any combinations thereof.

3. Plasticizers

The flexible, porous, dissolvable solid sheet may further comprise a plasticizer, in the amount ranging from about 0.1% to about 25%, from about 0.5% to about 20%, from about 1% to about 15%, or from 2% to 12%, by total weight of the solid sheet. Correspondingly, the wet pre-mixture used for forming such solid sheet may comprise from about 0.02% to about 20% of a plasticizer by weight of the wet pre-mixture, in one example from about 0.1% to about 10% of a plasticizer by weight of the wet pre-mixture, in one example from about 0.5% to about 5% of a plasticizer by weight of the wet pre-mixture.

Suitable plasticizers for use herein include, for example, polyols, copolyols, polycarboxylic acids, polyesters, dimethicone copolyols, and the like.

Examples of useful polyols include, but are not limited to: glycerin, diglycerin, ethylene glycol, polyethylene glycol (especially 200-600), propylene glycol, butylene glycol, pentylene glycol, glycerol derivatives (such as propoxylated glycerol), glycidol, cyclohexane dimethanol, hexanediol, 2,2,4-trimethylpentane-1,3-diol, pentaerythritol, urea, sugar alcohols (such as sorbitol, mannitol, lactitol, xylitol, maltitol, and other mono- and polyhydric alcohols), mono-, di- and oligo-saccharides (such as fructose, glucose, sucrose, maltose, lactose, high fructose corn syrup solids, and dextrins), ascorbic acid, sorbates, ethylene bisformamide, amino acids, and the like.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Examples of plasticizers include glycerin, ethylene glycol, polyethylene glycol, propylene glycol, or a mixture thereof.

4. Additional Ingredients

In addition to the above-described ingredients, e.g., the water-soluble polymer, the surfactant(s) and the plasticizer, the solid sheet may comprise one or more additional ingredients, depending on its intended application. Such one or more additional ingredients may be selected from the group consisting of fabric care actives, dishwashing actives, hard surface cleaning actives, beauty and/or skin care actives, personal cleansing actives, hair care actives, oral care actives, feminine care actives, baby care actives, a bittering agent and any combinations thereof. The solid sheet may comprise a bittering agent.

The solid sheet may further comprise other optional ingredients that are known for use or otherwise useful in compositions, provided that such optional materials are compatible with the selected essential materials described herein, or do not otherwise unduly impair product performance.

Non-limiting examples of product type examples that can be formed by the solid sheet include laundry detergent products, fabric softening products, hand cleansing products, hair shampoo or other hair treatment products, body cleansing products, shaving preparation products, dish cleaning products, personal care substrates containing pharmaceutical or other skin care actives, moisturizing products, sunscreen products, beauty or skin care products, deodorizing products, oral care products, feminine cleansing products, baby care products, fragrance-containing products, and so forth.

VI. Formulations of Coating Composition

The coating composition according to the present disclosure may comprise a non-aqueous liquid carrier, a thickening agent and solid particles. In some examples, the coating composition may have a viscosity of from about 1 cps to about 25,000 cps, from about 2 cps to about 10,000 cps, from about 3 cps to about 5,000 cps, or from about 1,000 cps to about 5,000 cps, as measured at about 20° C. and 1 s$^{-1}$. The viscosity values are measured using a Malvern Kinexus Lab+rheometer with cone and plate geometry (CP1/50 SR3468 SS), a gap width of 0.054 mm, a temperature of 20° C. and a shear rate of 1.0 reciprocal seconds for a period of 360 seconds.

1. Non-Aqueous Liquid Carrier

The coating composition may comprise from 1% to 99%, from 5% to 70%, from 20% to 50%, for example 1%, 2%, 3%, 4%, 5%, 6%, 7%, 8%, 9%, 10%, 15%, 20%, 25%, 30%, 35%, 40%, 45%, 50%, 55%, 60%, 65%, 70%/, 75%, 80%, 85%, 90%, 95% or any ranges therebetween, of the non-aqueous liquid carrier by total weight of the coating composition.

The non-aqueous liquid carrier may be selected from the group consisting of polyethylene glycol, polypropylene glycol, silicone, fatty acid, perfume oil, a non-ionic surfactant, an organic solvent and any combinations thereof. The non-aqueous liquid carrier may comprise a non-ionic surfactant. The non-ionic surfactant may be any appropriate non-ionic surfactant as listed hereinbefore. As another example, the non-ionic surfactant may comprise a $C_6$-$C_{20}$ linear or branched alkylalkoxylated alcohols (AA) having a weight average degree of alkoxylation ranging from 5 to 15, and/or a $C_{12}$-$C_{14}$ linear ethoxylated alcohols having a weight average degree of alkoxylation ranging from 7 to 9. In another example, the non-aqueous liquid carrier may comprise polyethylene glycol having a weight average molecular weight of less than 1000, less than 800, or less than 600.

2. Thickening Agent

The coating composition may comprise from 0.01% to 30%, from 0.05% to 20%, from 0.1% to 10%, for example 0.1%, 0.2%, 0.3%, 0.4%, 0.5%, 0.6%, 0.7%, 0.8%, 0.9%., 1.0%, 1.5%, 2.0%, 2.5%,3.0%, 3.5%, 4.0%, 4.5%, 5.0%, 6.0%, 7.0%, 8.0%, 9.0%, or any ranges therebetween, of the thickening agent silica by total weight of the coating composition.

Particularly, the thickening agent may be selected from the group consisting of silica, clays, polyacrylate thickeners, polyacrylamide thickeners, xanthan thickeners, guar gum, alginates ethoxylated cellulose, hydroxy propyl cellulose, hydroxy ethyl cellulose and any combinations thereof. The thickening agent may comprise silica, for example, fumed silica, and hydrophilic fumed silica (e.g. Aerosil A200). The hydrophilic fumed silica may comprise less than 10% residual salt by total weight of the silica and is capable of forming upon hydration swollen silica particles having a particle size distribution Dv50 of from 1 μm to 100 μm. Particularly, the fumed silica used herein may have a BET surface area of from around 30 to around 1000 m$^2$/g, from around 50 to around 500 m$^2$/g, for example 50, 100, 150, 200, 250, 300, 350, 400, 450 m$^2$/g or any ranges therebetween.

3. Solid Particles

The solid particles contained in the coating composition according to the present invention may comprise an oxidative dye compound, a pH modifier and/or a buffering agent, a radical scavenger, a chelant, a warming active, a color indicator, an anionic surfactant, an enzyme, a bleaching agent, an effervescent system or any combinations thereof.

In some examples, the solid particles have an average particle size of from 80 μm to 2000 μm. Particularly, the particles may have an average particle size of from 90 μm to 1000 μm, from 100 μm to 700 μm, from 110 μm to 500 μm, and from 120 μm to 400 μm, for example 100 μm, 200 μm, 300 μm, 400 μm, 500 μm, 600 μm, 700 μm, 800 μm, 900 μm, 1000 μm, 1100 μm, 1200 μm or any ranges therebetween.

The coating composition may comprise from 1% to 99%, from 5% to 90%, from 30% to 70%, for example 1%, 2%, 3%, 4%, 5%, 6%, 7%, 8%, 9%, 10%, 15%, 20%, 25%, 30%, 35%, 40%, 45%, 50%, 55%, 60/a, 65%, 70%, 75%, 80%, 85%, 90%, 95% or any ranges therebetween, of the solid particles by total weight of the coating composition.

a) Oxidative Dye Compounds

The solid particles contained in the coating composition according to the present invention may comprise an oxidative dye compound in the form of primary intermediates or couplers.

These compounds are well known in the art, and include aromatic diamines, aminophenols, aromatic diols and their derivatives (a representative but not exhaustive list of oxidation dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein. These are: 1,7-Dihydroxynaphthalene (1,7-NAPHTHALENEDIOL), 1,3-Diaminobenzene (m-PHENYLENEDIAMINE), 1-Methyl-2,5-diaminobenzene (TOLUENE-2,5-DIAMINE), 1,4-Diaminobenzene (p-PHENYLENEDIAMINE), 1,3-Dihydroxybenzene (RESORCINOL), 1,3-Dihydroxy-4-chlorobenzene, (4-CHLORORESORCINOL), 1-Hydroxy-2-aminobenzene, (o-AMINOPHENOL), 1-Hydroxy-3-aminobenzene (m-AMINOPHENOL), 1-Hydroxy-4-amino-benzene (p-AMINOPHENOL), 1-Hydroxynaphthalene (1-NAPHTHOL), 1,5-Dihydroxynaphthalene (1,5-NAPHTHALENEDIOL), 2,7-dihydroxynaphthalene (2,7-NAPHTHALENEDIOL) 1-Hydroxy-2,4-diaminobenzene (4-DIAMINOPHENOL), 1,4-Dihydroxybenzene (HYDROQUINONE), 1-Hydroxy-4-methylaminobenzene (p-METHYLAMINOPHENOL), 6-Hydroxybenzo-morpholine (HYDROXYBENZOMORPHOLINE), 1-Methyl-2-hydroxy-4-aminobenzene (4-AMINO-2-HYDROXY-TOLUENE), 3,4-Diaminobenzoic acid (3,4-DIAMINOBENZOIC ACID), 1-Methyl-2-hydroxy-4-(2'-hydroxyethyl)aminobenzene (2-METHYL-5-HYDROXY-ETHYLAMINO-PHENOL), 1,2,4-Trihydroxybenzene (1,2,4-TRIHYDROXYBENZENE), 1-Phenol-3-methylpyrazol-5-on (PHENYLMETHYLPYRAZOLONE), 1-(2'-Hydroxyethyloxy)-2,4-diaminobenzene (2,4-DIAMINOPHENOXY-ETHANOL HCL), 1-Hydroxy-3-amino-2,4-dichlorobenzene (3-AMINO-2,4-DICHLORO-PHENOL), 1,3-Dihydroxy-2-methylbenzene (2-METHYLRESORCINOL), 1-Amino-4-bis-(2'-hydroxyethyl)aminobenzene (N,N-BIS(2-HYDROXY-ETHYL)-p-PHENYLENE-DIAMINE), 2,4,5,6-Tetraaminopyrimidine (HC Red 16), 1-Hydroxy-3-methyl-4-aminobenzene (4-AMINO-m-CRESOL), 1-Hydroxy-2-amino-5-methyl-benzene (6-AMINO-m-CRESOL), 1,3-Bis-(2,4-Diaminophenoxy)propane (1,3-BIS-(2,4-DIAMINO-PHENOXY)-PROPANE),1-(2'-Hydroxyethyl)-2,5-diaminobenzene (HYDROXYETHYL-p-PHENYLENE DIAMINE SULPHATE), 1-Methoxy-2-amino-4-(2'-hydroxyethylamino) benzene, (2-AMINO-4-HYDROXYETHYLAMINOANISOLE) I-Hydroxy-2-methyl-5-amino-6-chlorobenzene (5-AMINO-6-CHLORO-o-CRESOL), 1-Hydroxy-2-amino-6-methylbenzene (6-AMINO-o-CRESOL), 1-(2'-Hydroxyethyl)-amino-3,4-methylenedioxybenzene (HYDROXYETHYL-3,4-METHYLENEDIOXY-ANILINE HCl), 2,6-Dihydroxy-3,4-dimethylpyridine (2,6-DIHYDROXY-3,4-DIMETHYLPYRIDINE), 3,5-Diamino-2,6-dimethoxypyridine (2,6-DIMETHOXY-3,5-PYRIDINEDIAMINE), 5,6-Dihydroxyindole (,DIHYDROXY-INDOLE), 4-Amino-2-aminomethylphenol (2-AMINOETHYL-p-AMINO-PHENOL HCl), 2,4-Diamino-5-methylphenetol (2,4-DIAMINO-5-METHYL-PHENETOLE HCl), 2,4-Diamino-5-(2'-hydroxyethyloxy) toluene (2,4-DIAMINO-5-METHYLPHENOXYETHANOL HCl), 5-Amino-4-chloro-2-methylphenol (5-AMINO-4-CHLORO-o-CRESOL), 4-Amino-1-hydroxy-2-(2'-hydroxyethylaminomethyl)benzene HYDROXYETHYLAMINOMETHYL-p-AMINO PHENOL HCl), 4-Amino-1-hydroxy-2-methoxymethylbenzene (2-METHOXYMETHYL-p-AMINOPHENOL HCl), 1,3-Bis(N(2-Hydroxyethyl)N(4-amino-phenyl)amino)-2-propanol (HYDROXYPROPYL-BIS-(N-HYDROXYETHYL-p-PHENYLENEDIAMINE)HCL), 6-Hydorxyindole (6-HYDROXY-INDOLE), 2,3-Indolinedione (ISATIN), 3-Amino-2-methylamino-6-methoxypyridine (HC BLUE NO. 7), 1-Phenyl-3-methyl-5-pyrazolone-2,4-dihydro-5,2-phenyl-3H-pyrazole-3-one, 2-Amino-3-hydroxypyridine (2-AMINO-3-HYDROXYPYRIDINE), 5-Amino-salicylic acid, 1-Methyl-2,6-bis(2-hydroxy-ethylamino)benzene (2,6-HYDROXYETHYLAMINO-TOLUENE), 4-Hydroxy-2,5,6-triaminopyrimidine (2,5,6-TRIAMINO-4-PYRIMIDINOL SULPHATE), 2,2'-[1,2-Ethanediyl-bis-(oxy-2,1-ethanediyloxy)]-bis-benzene-1,4-diamine (PEG-3,2',2'-DI-p-PHENYLENEDIAMINE), 5,6-Dihydroxyindoline (DIHYDROXYINDOLINE), N,N-Dimethyl-3-ureidoaniline (m-DIMETHYL-AMINO-PHENYLUREA), 2,4-Diamino-5-fluortoluenesulfatehydrate (4-FLUORO-6-METHYL-m-PHENYLENEDIAMINE SULPHATE) and 1-Acetoxy-2-methylnaphthalene (1-HYDROXYYETHYL-4,5-DIAMINOPYRAZOLE SULPHATE). These can be used in the molecular form or in the form of peroxide-compatible salts.

b) pH Modifiers and Buffering Agents

The solid particles contained in the coating composition according to the present invention may comprise a pH modifier and/or a buffering agent in an amount that is sufficiently effective to adjust the pH of the composition to fall within a range from about 3 to about 13, in some examples from about 8 to about 12, and even from about 8 to about 11. Suitable pH modifiers and/or buffering agents for use herein include, but are not limited to: ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, like sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

c) Radical Scavenger System

The solid particles contained in the coating composition according to the present invention may comprise a radical scavenger in a sufficient amount to reduce damage to the hair during an oxidative bleaching or coloring process. The radical scavenger may be selected such that it is not an identical species as the alkalizing agent. The radical scavengers may be selected from the classes of alkanolamines, amino sugars, amino acids and mixtures thereof, and may include, but are not limited to: monoethanolamine, 3-amino-1-propanol, 4-amino-1-butanol,5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other radical scavenger compounds can include benzylamine, glutamic acid, imidazole, di-tert-butylhydroxytoluene, hydroquinone, catechol and mixtures thereof.

d) Chelants

The solid particles contained in the coating composition according to the present invention may comprise a chelant in an amount sufficient to reduce the amount of metals available to interact with formulation components. Suitable chelants for use herein include but are not limited to: diamine- N,N'-dipolyacid, monoamine monoamide-N,N'-dipolyacid, and N,N'-bis(2-hydroxybenzyl)ethylenediamine-N,N'-diacetic acid chelants (ex. EDDS (ethylenediaminedisuccinic acid)), carboxylic acids (ex. aminocarboxylic acids), phosphonic acids (ex. aminophosphonic acids) and polyphosphoric acids (in particular straight polyphosphoric acids), their salts and derivatives.

e) Warming Actives

The solid particles contained in the coating composition according to the present invention may comprise a warming active. The warming actives may include heat generating agents, or heat generating powders which release heat via exothermic reactions (heat producing) when they are mixed with water during application. The heat generating agents include, but are not limited to, inorganic salts, glycols, finely divided solid adsorbent materials, and iron redox systems. In one example the warming actives are selected from the group consisting of anhydrous inorganic salts including, but not limited to calcium chloride, magnesium chloride, calcium oxide, magnesium sulphate, aluminium sulphate and combinations thereof. In yet another example the warming actives are selected from the group consisting of anhydrous calcium chloride, anhydrous magnesium chloride, anhydrous magnesium sulphate, and combinations thereof.

f) Color Indicators

The solid particles contained in the coating composition according to the present invention may comprise a color indicator. Such color indicators can be present in an amount sufficient to result in a visual color change when the indicator is contacted with water. The term "visual color change" refers to a color change that can be detected by the human eye, either alone, or with the aid of an energy source such as a black light. The color indicators can include, but are not limited to, those selected from the group consisting of pH indicators, photoactive pigments, thermochromatic pigments, and combinations thereof.

In one example the color change is a pH sensitive color changing component. The color indicators can be selected from the group consisting of bromocresol green, phenolphthalein, a-cresolphthalein, thymolphthalein, coumarin, 2,3-dioxyxanthone, coumeric acid, 6,8-dinitro-2,4(1H) quinazolinedione, ethyl-bis (2,4-dimethylphenyl) ethanoate, and combinations thereof.

g) Enzyme

The solid particles contained in the coating composition according to the present invention may comprise an enzyme. Any enzyme known in the art can be used in the coating composition. An enzyme may be selected from the group consisting of proteases, amylases, cellulases, lipases, xyloglucanases, pectate lyases, mannanases, cutinases, and any combinations thereof.

h) Bleaching Agent

The solid particles contained in the coating composition according to the present invention may comprise a bleaching agent. The bleaching agent may be selected from the group consisting of a source of available oxygen, a bleach activator, a pre-formed peracid, a bleach catalyst, a reducing bleach, and any combinations thereof. Particularly, the bleaching agent may be in a form of particles that have an average particle size of from 80 μm to 2000 μm, from 100 μm to 1500 μm, for example 100 μm, 200 μm, 300 μm, 400 μm, 500 μm, 600 μm, 700 μm, 800 sim, 900 μm, 1000 μm, 1100 μm, 1200 μm or any ranges therebetween. The particle size may bring about an improved dissolution profile and/or an improved leakage performance.

The source of available oxygen (AvOx) may be a source of hydrogen peroxide that is selected from the group consisting of percarbonate salts, perborate salts, persulfate salts and any combinations thereof. The source of available oxygen may be at least partially coated, or even completely coated, by a coating ingredient such as a carbonate salt, a sulphate salt, a silicate salt, borosilicate, or any mixture thereof, including mixed salts thereof. Suitable percarbonate salts can be prepared by a fluid bed process or by a crystallization process. Suitable perborate salts include sodium perborate mono-hydrate (PB1), sodium perborate tetra-hydrate (PB4), and anhydrous sodium perborate which is also known as fizzing sodium perborate. Other suitable sources of AvOx include persulphate, such as oxone. Another suitable source of AvOx is hydrogen peroxide The bleach activator may be selected from the group consisting of tetraacetylethylenediamine (TAED); oxybenzene sulphonates such as nonanoyl oxybenzene sulphonate (NOBS), caprylamidononanoyl oxybenzene sulphonate (NACA-OBS), 3,5,5-trimethyl hexanoyloxybenzene sulphonate (Iso-NOBS), dodecyl oxybenzene sulphonate (LOBS), and any mixture thereof; caprolactams; pentaacetate glucose (PAG); nitrile quaternary ammonium; imide bleach activators, such as N-nonanoyl-N-methyl acetamide; and any mixture thereof.

The pre-formed peracid may be N,N-pthaloylamino peroxycaproic acid (PAP).

The bleach catalyst may be selected from the group consisting of oxaziridinium-based bleach catalysts, transition metal bleach catalysts, and any combinations thereof.

A suitable oxaziridinium-based bleach catalyst has the formula:

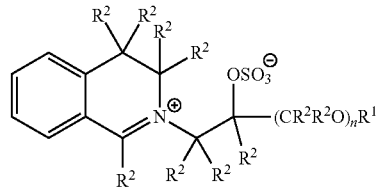

wherein: $R^1$ is selected from the group consisting of: H, a branched alkyl group containing from 3 to 24 carbons, and a linear alkyl group containing from 1 to 24 carbons; $R^1$ can be a branched alkyl group comprising from 6 to 18 carbons, or a linear alkyl group comprising from 5 to 18 carbons, $R^1$ can be selected from the group consisting of: 2-propylheptyl, 2-butyloctyl, 2-pentylnonyl, 2-hexyldecyl, n-hexyl, n-octyl, n-decyl, n-dodecyl, n-tetradecyl, n-hexadecyl, n-octadecyl, iso-nonyl, iso-decyl, iso-tridecyl and iso-pentadecyl; $R^2$ is independently selected from the group consisting of: H, a branched alkyl group comprising from 3 to 12 carbons, and a linear alkyl group comprising from 1 to 12 carbons; optionally $R^2$ is independently selected from H and methyl groups; and n is an integer from 0 to 1.

Transition metal bleach catalyst may comprise copper, iron, titanium, ruthenium, tungsten, molybdenum, and/or manganese cations. Suitable transition metal bleach catalysts are manganese-based transition metal bleach catalysts.

The reducing bleach may be sodium sulphite and/or thiourea dioxide (TDO).

Particularly, the coating composition may comprise from 1% to 99%, from 10% to 80%, from 30% to 70%, for example 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or any ranges therebetween, of the bleaching agent by total weight of the coating composition. More particularly, the coating composition may comprise from 1% to 99%, from 10% to 80%, from 30% to 70%, for example 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or any ranges therebetween, of the source of available oxygen by total weight of the coating composition, and/or the coating composition may comprise from 1% to 99%, from 10% to 80%, from 30% to 70%, for example 1%, 2%, 3%,4%, 5%, 6%, 7%, 8%, 9%, 10%, 15%, 20%, 25%, 30%, 35%,40%, 45%, 50%, 55%, 60%, 65%, 70%, 75%, 80%, 85%, 90%, 95% or any ranges therebetween, of the bleach activator by total weight of the coating composition.

i) Effervescent System

The solid particles contained in the coating composition according to the present invention may comprise an effervescent system. Any effervescent system known in the art can be used in the coating composition. One example of an effervescent system comprises an acid source and an alkali source, capable of reacting with each other in the presence of water to produce a gas.

The acid source component may be any organic, mineral or inorganic acid, or a derivative thereof, or a combination thereof. The acid source component may comprise an organic acid. The acid compound may be substantially anhydrous or non-hygroscopic and the acid may be water-soluble. The acid source may be overdried.

Suitable acid source components include citric acid, malic acid, tartaric acid, fumaric acid, adipic acid, maleic acid, aspartic acid, glutaric acid, malonic acid, succinic acid, boric acid, benzoic acid, oleic acid, citramalic acid, 3-chetoglutaric acid, or any combination thereof. Citric acid, maleic or tartaric acid may also be used. The acid source may be further coated with a coating such as a salt. In an example, citric acid as the acid source may be coated with sodium citrate.

Any alkali source which has the capacity to react with the acid source to produce a gas may be present in the particle, which may be any gas known in the art, including nitrogen, oxygen and carbon dioxide gas. An alkali source may include those selected from the group consisting of a carbonate salt, a bicarbonate salt, a sesquicarbonate salt and any combinations thereof. The alkali source may be substantially anhydrous or non-hydroscopic. The alkali source may be overdried.

The gas may be carbon dioxide, and therefore the alkali source may be a source of carbonate, which can be any source of carbonate known in the art. One example of a carbonate source is a carbonate salt. Examples of suitable carbonates are the alkaline earth and alkali metal carbonates, including sodium or potassium carbonate, bicarbonate and sesqui-carbonate and any combinations thereof with ultra-fine calcium carbonate or sodium carbonate. Alkali metal percarbonate salts are also suitable sources of carbonate species, which may be present combined with one or more other carbonate sources.

4. Additional Ingredients

In addition to the above-described ingredients, the coating composition may comprise one or more additional ingredients, depending on its intended application. Such one or more additional ingredients may be selected from the group consisting of fabric care actives, dishwashing actives, hard surface cleaning actives, beauty and/or skin care actives, personal cleansing actives, hair care actives, oral care actives, feminine care actives, baby care actives, a bittering agent and any combinations thereof.

Particularly, the coating composition may further comprise an additional ingredient selected from the group consisting of a softening agent, silicone, an emulsifier, an enzyme, a colorant, a brightener, a dye transfer inhibiting agent, a deposition aid, an anti-microbial agent, a chelant, a non-film forming polymer, an anti-foamer, a defoamer, and any combinations thereof.

The coating composition may comprise from 0.0001% to 99/, from 1% to 95%, from 10% to 80%, for example 0.001%, 0.01%, 0.1%, 1%, 2%, 3%, 4%, 5%, 8%, 10%, 15%, 20%, 25%, 30%, 35%, 40%, 45%, 50%, 55%, 60%, 65%, 70%, 75%, 80%, 85%, 90%, 95% or any ranges therebetween, of the additional ingredient by total weight of the coating composition.

VII. Conversion of Multiple Solid Sheets and Coating Composition into Multilayer Dissolvable Solid Articles Containing Coating Composition Once the flexible, dissolvable, porous solid sheet is formed, as described hereinabove, two or more of such sheets can be treated by applying the coating composition that comprises a bleaching agent and then combined to form dissolvable solid articles of any desirable three-dimensional shapes, including but not limited to: spherical, cubic, rectangular, oblong, cylindrical, rod, sheet, flower-shaped, fan-shaped, star-shaped, disc-shaped, and the like. The sheets can be combined and/or treated by any means known in the art, examples of which include but are not limited to, chemical means, mechanical means, and combinations thereof. Such combination and/or treatment steps are hereby collectively referred to as a "conversion" process, i.e., which functions to convert two or more flexible, dissolvable, porous sheets into a dissolvable solid article containing a coating composition.

It has been a surprising and unexpected discovery that the bleaching agent contained in the multilayer solid articles shows significantly improved stability compared to a bleaching agent alone stored under the same conditions. It has been another surprising and unexpected discovery that the bleaching agent contained in the multilayer solid articles shows significantly improved anti-microorganism effect.

Furthermore, the multilayer dissolvable solid articles may be characterized by a maximum dimension D and a minimum dimension z (which is perpendicular to the maximum dimension), while the ratio of D/z (hereinafter also referred to as the "Aspect Ratio") ranges from 1 to about 10, from about 1.4 to about 9, from about 1.5 to about 8, from about 2 to about 7. Note that when the Aspect Ratio is 1, the dissolvable solid article has a spherical shape. When the Aspect Ratio is about 1.4, the dissolvable solid article has a cubical shape. The multilayer dissolvable solid article may have a minimal dimension z that is greater than about 3 mm but less than about 20 cm, from about 4 mm to about 10 cm, from about 5 mm to about 30 mm.

The above-described multilayer dissolvable solid article may comprise more than two of such flexible, dissolvable, porous sheets. For example, it may comprise from about 3 to about 50, from about 4 to about 40, from about 5 to about 30, for example 6, 7, 8, 9, 10, 15, 20, 25, 30 or any ranges therebetween, of the flexible, dissolvable, porous sheets. The improved OCF structures in the flexible, dissolvable, porous sheets made according to the present invention allow stacking of many sheets (e.g., 15-40) together, while still providing a satisfactory overall dissolution rate for the stack.

The multilayer dissolvable solid article may comprise from 15 to 40 layers of the above-described flexible, dissolvable, porous sheets and have an aspect ratio ranging from about 2 to about 7.

Particularly, the coating composition containing the bleaching agent may be applied between individual sheets of the multilayer dissolvable solid article by any appropriate means, e.g., by spraying, sprinkling, dusting, coating, spreading, dipping, injecting, rolling, or even vapor deposition. More particularly, the coating composition may be applied on one or both of contacting surfaces of adjacent sheets in the stack. In order to avoid interference of the coating composition with the cutting seal or edge seal near the peripherals of the individual sheets, the coating composition may be applied in a central region on each of the applied surfaces of the respective sheets, which may be defined as a region that is spaced apart from the peripherals of such adjacent sheets by a distance that is at least 5%, at least 10%, at least 15%, at least 20%, of the maximum Dimension D. Said coating composition may also be applied throughout the applied surfaces of the respective sheets, wherein the applied area may account for at least 90%, 95%, 98%, 99% of the total area of the applied surfaces.

The coating composition may be applied on one or both contacting surfaces of any adjacent sheets in the solid article. The coating composition may be applied on one or both contacting surfaces of middle two sheets in the stack. The coating composition may be applied on one or both of contacting surfaces of any two adjacent sheets in the stack excluding the two outermost sheets.

The dissolvable solid article may comprise a first group of one or more sheets and a second group of one or more sheets in which the coating composition is present on at least one surface of at least one of said first group of one or more sheets but not on any one surface of said second group of one or more sheets, wherein the coating composition comprises a source of available oxygen that may be selected from the group consisting of percarbonate salts, perborate salts, persulfate salts, and any combinations thereof and wherein each sheet in said second group of one or more sheets comprises a bleach activator that may be selected from the group consisting of tetraacetylethylenediamine (TAED), oxybenzene sulphonates, caprolactams; pentaacetate glucose (PAG), nitrile quaternary ammonium, imide bleach activators and any combinations thereof. In this case, the source of available oxygen is separated from the bleach activator so that the stability of the source of available oxygen may be further improved. Particularly, the first group of one or more sheets may comprise at least two sheets, or at least four sheets, stacked together in which the coating composition is present on one or both contacting surfaces of middle two sheets within the first group of one or more sheets. Further, the second group of one or more sheets may be located on the bottom or top of the first group of one or more sheets or both.

The term of "middle two sheets" as used herein means the two adjacent sheets that are located in the middle of the sequence of sheets stacked together. Particularly, if the total number of sheets is an odd number (e.g., 7), middle two sheets include the sheet that is located in the middle and any of two adjacent sheets thereof (e.g., the $3^{th}$ and $4^{th}$ sheets or the $4^{th}$ and $5^{th}$ sheets); and if the total number of sheets is an even number (e.g., 6), middle two sheets include the two sheets that are located in the middle (e.g., the $3^{th}$ and $4^{th}$ sheets).

Particularly, the weight ratio of the coating composition over the solid sheets in the multilayer dissolvable solid article may be from 0.1 to 10, from 0.1 to 7, from 0.5 to 5, and from 1 to 3, for example 0.5, 0.6, 0.7, 0.8, 0.9, 1, 1.2, 1.5, 2, 2.5, 3, 3.5, 4, 4.5, 5 or any ranges therebetween.

Figure 7A:
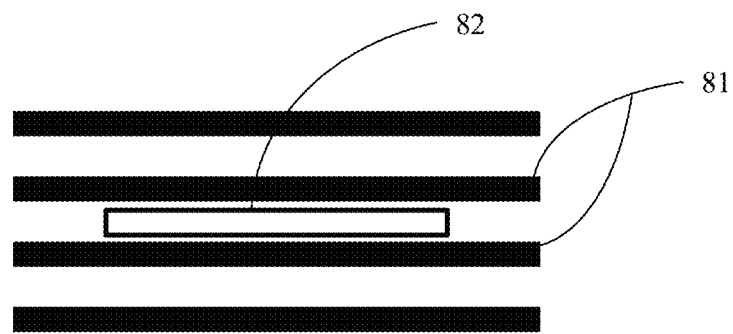
FIG. 7A shows an illustrative diagram of an example of the dissolvable solid article having multiple flexible, porous sheets according to the present disclosure, in which a coating composition comprising a bleaching agent is applied between two adjacent sheets.

FIG. 7A shows an exemplary multilayer dissolvable solid article according to the present disclosure, in which a coating composition 82 comprising a bleaching agent (e.g. a percarbonate salt) is applied between the middle two sheets 81.

Figure 7B:
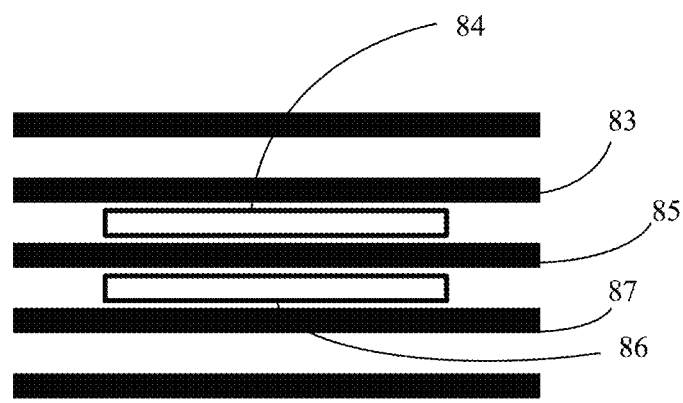
FIG. 7B shows an illustrative diagram of another example of the dissolvable solid article having multiple flexible, porous sheets according to the present disclosure, in which a first coating composition comprising a source of available oxygen is applied between two adjacent sheets and a second coating composition comprising a bleach activator is applied between another two adjacent sheets.

FIG. 7B shows another exemplary multilayer dissolvable solid article according to the present disclosure, in which a first coating composition 84 comprising a source of available oxygen (e.g. a percarbonate salt) is applied between the sheets 83 and 85 and a second coating composition 86 comprising a bleach activator (e.g. TAED) is applied between the sheets 85 and 87.

Figure 7C:
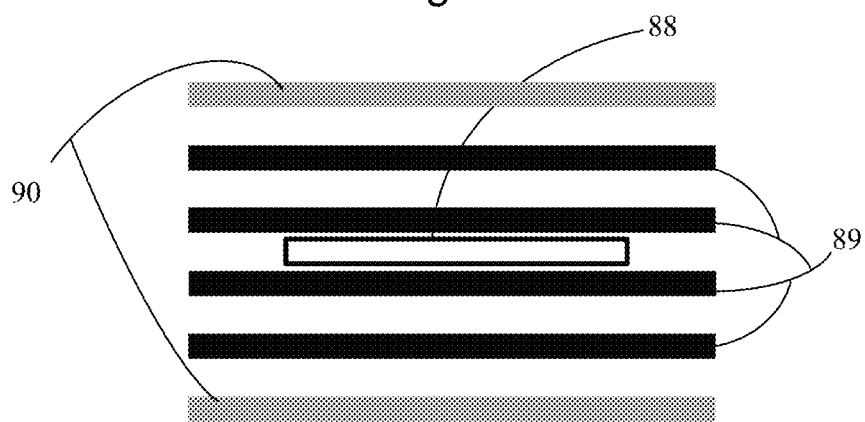
FIG. 7C shows an illustrative diagram of another example of the dissolvable solid article having multiple flexible, porous sheets according to the present disclosure, in which the solid article comprises a first group of sheets, a second group of sheets, and a coating composition comprising a source of available oxygen which is applied between two adjacent sheets within the first group of sheets.

FIG. 7C shows another exemplary multilayer dissolvable solid article according to the present disclosure, in which the article comprises a first group of sheets 89 (4 solid sheets) and a second group of sheets 90 (2 solid sheets in total) and a coating composition 88 comprising a source of available oxygen (e.g. a percarbonate salt). The coating composition 88 is applied between the middle two sheets within the first group of sheets 89 which may comprise no bleach activator. The second group of sheets 90 comprises a bleach activator (e.g. TAED) and is located on the top and the bottom of the first group of sheets 89.

Test Methods

Test 1: Scanning Electron Microscopic (SEM) Method for Determining Surface Average Pore Diameter of the Sheet Article A Hitachi TM3000 Tabletop Microscope (S/N: 123104-04) is used to acquire SEM micrographs of samples. Samples of the solid sheet articles are approximately 1 cm×1 cm in area and cut from larger sheets. Images are collected at a magnification of 50X, and the unit is operated at 15 kV. A minimum of 5 micrograph images are collected from randomly chosen locations across each sample, resulting in a total analyzed area of approximately 43.0 mm$^2$ across which the average pore diameter is estimated.

The SEM micrographs are then firstly processed using the image analysis toolbox in Matlab. Where required, the images are converted to grayscale. For a given image, a histogram of the intensity values of every single pixel is generated using the 'imhist' Matlab function. Typically, from such a histogram, two separate distributions are obvious, corresponding to pixels of the brighter sheet surface and pixels of the darker regions within the pores. A threshold value is chosen, corresponding to an intensity value between the peak value of these two distributions. All pixels having an intensity value lower than this threshold value are then set to an intensity value of 0, while pixels having an intensity value higher are set to 1, thus producing a binary black and white image. The binary image is then analyzed using ImageJ (https://imagej.nih.gov, version 1.52a), to examine both the pore area fraction and pore size distribution. The scale bar of each image is used to provide a pixel/mm scaling factor. For the analysis, the automatic thresholding and the analyze particles functions are used to isolate each pore. Output from the analyze function includes the area fraction for the overall image and the pore area and pore perimeter for each individual pore detected.

Average Pore Diameter is defined as $D_A50$: 50% of the total pore area is comprised of pores having equal or smaller hydraulic diameters than the $D_A50$ average diameter.

Hydraulic diameter='4*Pore area (m$^2$)/Pore perimeter (m)'.

It is an equivalent diameter calculated to account for the pores not all being circular.

Test 2: Micro-Computed Tomographic (μCT) Method for Determining Overall or Regional Average Pore Size and Average Cell Wall Thickness of the Open Cell Foams (OCF)

Porosity is the ratio between void-space to the total space occupied by the OCF. Porosity can be calculated from μCT scans by segmenting the void space via thresholding and determining the ratio of void voxels to total voxels. Similarly, solid volume fraction (SVF) is the ratio between solid-space to the total space, and SVF can be calculated as the ratio of occupied voxels to total voxels. Both Porosity and SVF are average scalar-values that do not provide structural information, such as, pore size distribution in the height-direction of the OCF, or the average cell wall thickness of OCF struts.

To characterize the 3D structure of the OCFs, samples are imaged using a μCT X-ray scanning instrument capable of acquiring a dataset at high isotropic spatial resolution. One example of suitable instrumentation is the SCANCO system model 50 μCT scanner (Scanco Medical AG, Bruttisellen, Switzerland) operated with the following settings: energy level of 45 kVp at 133 μA; 3000 projections; 15 mm field of view; 750 ms integration time; an averaging of 5; and a voxel size of 3 μm per pixel. After scanning and subsequent data reconstruction is complete, the scanner system creates a 16 bit data set, referred to as an ISQ file, where grey levels reflect changes in x-ray attenuation, which in turn relates to material density. The ISQ file is then converted to 8 bit using a scaling factor.

Scanned OCF samples are normally prepared by punching a core of approximately 14 mm in diameter. The OCF punch is laid flat on a low-attenuating foam and then mounted in a 15 mm diameter plastic cylindrical tube for scanning. Scans of the samples are acquired such that the entire volume of all the mounted cut sample is included in the dataset. From this larger dataset, a smaller sub-volume of the sample dataset is extracted from the total cross section of the scanned OCF, creating a 3D slab of data, where pores can be qualitatively assessed without edge/boundary effects.

To characterize pore-size distribution in the height-direction, and the strut-size, Local Thickness Map algorithm, or LTM, is implemented on the subvolume dataset. The LTM Method starts with a Euclidean Distance Mapping (EDM) which assigns grey level values equal to the distance each void voxel is from its nearest boundary. Based on the EDM data, the 3D void space representing pores (or the 3D solid space representing struts) is tessellated with spheres sized to match the EDM values. Voxels enclosed by the spheres are assigned the radius value of the largest sphere. In other words, each void voxel (or solid voxel for struts) is assigned the radial value of the largest sphere that that both fits within the void space boundary (or solid space boundary for struts) and includes the assigned voxel.

The 3D labelled sphere distribution output from the LTM data scan can be treated as a stack of two dimensional images in the height-direction (or Z-direction) and used to estimate the change in sphere diameter from slice to slice as a function of OCF depth. The strut thickness is treated as a 3D dataset and an average value can be assessed for the whole or parts of the subvolume. The calculations and measurements were done using AVIZO Lite (9.2.0) from Thermo Fisher Scientific and MATLAB (R2017a) from Mathworks.

Test 3: Percent Open Cell Content of the Sheet Article

The Percent Open Cell Content is measured via gas pycnometry. Gas pycnometry is a common analytical technique that uses a gas displacement method to measure volume accurately. Inert gases, such as helium or nitrogen, are used as the displacement medium. A sample of the solid sheet article is sealed in the instrument compartment of known volume, the appropriate inert gas is admitted, and then expanded into another precision internal volume. The pressure before and after expansion is measured and used to compute the sample article volume.

ASTM Standard Test Method D2856 provides a procedure for determining the percentage of open cells using an older model of an air comparison pycnometer. This device is no longer manufactured. However, one can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials. For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the open cell volume as measured by the Accupyc, according to the following equation:

$$\text{Open cell percentage} = \text{Open cell volume of sample} / \text{Geometric volume of sample} * 100$$

It is recommended that these measurements be conducted by Micromeretics Analytical Services, Inc. (One Micromeritics Dr, Suite 200, Norcross, GA 30093). More information on this technique is available on the Micromeretics Analytical Services web sites (www.particletesting.com or www.micromeritics.com), or published in "Analytical Methods in Fine particle Technology" by Clyde Orr and Paul Webb.

Test 4: Final Moisture Content of the Sheet Article

Final moisture content of the solid sheet article is obtained by using a Mettler Toledo HX204 Moisture Analyzer (S/N B706673091). A minimum of 1 g of the dried sheet article is placed on the measuring tray. The standard program is then executed, with additional program settings of 10 minutes analysis time and a temperature of 110° C.

Test 5: Thickness of the Sheet Article

Thickness of the flexible, porous, dissolvable solid sheet article is obtained by using a micrometer or thickness gage, such as the Mitutoyo Corporation Digital Disk Stand Micrometer Model Number IDS-1012E (Mitutoyo Corporation, 965 Corporate Blvd, Aurora, IL, USA 60504). The micrometer has a 1-inch diameter platen weighing about 32 grams, which measures thickness at an application pressure of about 0.09 psi (6.32 gm/cm$^2$).

The thickness of the flexible, porous, dissolvable solid sheet article is measured by raising the platen, placing a section of the sheet article on the stand beneath the platen, carefully lowering the platen to contact the sheet article, releasing the platen, and measuring the thickness of the sheet article in millimeters on the digital readout. The sheet article should be fully extended to all edges of the platen to make sure thickness is measured at the lowest possible surface pressure, except for the case of more rigid substrates which are not flat.

Test 6: Basis Weight of the Sheet Article

Basis Weight of the flexible, porous, dissolvable solid sheet article is calculated as the weight of the sheet article per area thereof (grams/m$^2$). The area is calculated as the projected area onto a flat surface perpendicular to the outer edges of the sheet article. The solid sheet articles are cut into sample squares of 10 cm×10 cm, so the area is known. Each of such sample squares is then weighed, and the resulting weight is then divided by the known area of 100 cm² to determine the corresponding basis weight.

For an article of an irregular shape, if it is a flat object, the area is thus computed based on the area enclosed within the outer perimeter of such object. For a spherical object, the area is thus computed based on the average diameter as $3.14 \times (diameter/2)^2$. For a cylindrical object, the area is thus computed based on the average diameter and average length as diameter x length. For an irregularly shaped three-dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (shaded-in for contrast) including a scale and using image analysis techniques.

Test 7: Density of the Sheet Article

Density of the flexible, porous, dissolvable solid sheet article is determined by the equation: Calculated Density=Basis Weight of porous solid/(Porous Solid Thickness×1,000). The Basis Weight and Thickness of the dissolvable porous solid are determined in accordance with the methodologies described hereinabove.

Test 8: Specific Surface Area of the Sheet Article

The Specific Surface Area of the flexible, porous, dissolvable solid sheet article is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeretics Analytical Services, Inc. (One Micromeritics Dr, Suite 200, Norcross, GA 30093). More information on this technique is available on the Micromeretics Analytical Services web sites (www.particletesting.com or www.micromeritics.com), or published in a book, "Analytical Methods in Fine Particle Technology", by Clyde Orr and Paul Webb.

Test 9: Dissolution Rate of the Sheet Article

The dissolution rate of dissolvable sheets or solid articles is measured as follows:
1. 400 ml of deionized water at room temperature (25° C.) is added to a 1 L beaker, and the beaker is then placed on a magnetic stirrer plate.
2. A magnetic stirrer bar having length 23 mm and thickness of 10 mm is placed in the water and set to rotate at 300 rpm.
3. A Mettler Toledo S230 conductivity meter is calibrated to 1413 µS/cm and the probe placed in the beaker of water.
4. For each experiment, the number of samples is chosen such that a minimum of 0.2 g of sample is dissolved in the water.
5. The data recording function on the conductivity meter is started and the samples are dropped into the beaker. For 5 seconds a flat steel plate with diameter similar to that of the glass beaker is used to submerge the samples below the surface of the water and prevent them from floating to the surface.
6. The conductivity is recorded for at least 10 minutes, until a steady state value is reached.
7. In order to calculate the time required to reach 95% dissolution, a 10 second moving average is firstly calculated from the conductivity data. The time at which this moving average surpassed 95% of the final steady state conductivity value is then estimated and taken as the time required to achieve 95% dissolution.

Test 10: Stability of the Coating Composition

Coating compositions are prepared by adding all ingredients together into a 250 ml plastic beaker and mixing at 1000 RPM for 1 minute using an overhead stirrer. Then, in order to determine stability of the coating compositions, each formulation is poured into a 30 ml glass vial until the vial is completely filled. The vial is sealed and then stored upright for 24 hours under room temperature. After 24 hours, each vial is visually inspected for liquid-solid separation. The mixture is deemed unstable if a liquid layer with vertical length of at least 5 mm is measured.

Test 11: Leakage of the Coating Composition

Leakage of coating compositions between adjacent solid sheet layers after adding the coating composition is assessed by using a drop test. The solid sheets used in this test prepared according to the method in the Section III: PROCESS OF MAKING SOLID SHEETS are firstly conditioned by placing them in a temperature and humidity controlled room, with temperature and humidity controlled in the range 23 to 24.5° C. and 41 to 45% relative humidity respectively, for a minimum of 1 hour. The sheets are laid out individually and not stacked upon one another.

10×10 cm square samples of foam sheets are then cut out from the larger sheets by utilizing a paper guillotine. All four edges of the 10×10 cm square are cut by utilizing the paper guillotine. None of the existing edges of the larger sheet stack are used as edges of the smaller 10×10 cm square.

The coating composition is then added to the center of one of the 10×10 cm square samples, and a second 10×10 cm sample then placed on top of the first sample, such that the two sheet layers are orientated in toe-to-toe configuration. No excessive pressure is applied to the sheet stack during the testing, wherein the excessive pressure is defined as any pressure resulting in a 0.05 mm or greater thickness change of the sheet. The 10×10 cm sample is further cut by using the paper guillotine to a smaller 5×5 cm sample, in which the coating composition is remained in the center of the 5×5 cm sample.

The drop test is carried out as follows. A plastic thumb forceps is utilized to place the test sample (i.e. 5×5 cm sample) 1.0 meter above a solid surface such as the floor or a tabletop. The sample is orientated such that one of the edges exposed by cutting is parallel to the solid surface. The sample is then released and allowed to fall. After dropping to the solid surface, the edges of the two sheet layers may separate due to the presence of the coating composition, resulting in leakage of the coating composition. As such, the percentage of adhesion can be used as a 'leakage score' to characterize the leakage degree of the coating composition. The 'leakage score' ranging from 0 to 5 is assigned to each sample, according to the following criteria.

0—Less than 5% of the two sheet layer edges are in contact with one another
1—Exactly 5% or between 5 to 25% of the two sheet layer edges are adhered to one another
2—Exactly 25% or between 25% to 50% of the two sheet layer edges are adhered to one another
3—Exactly 50% or between 50% to 75% of the two sheet layer edges are adhered to one another
4—Exactly 75% or between 75% to 95% of the two sheet layer edges are adhered to one another
5—Exactly 95% or greater than 95% of the two sheet layer edges are adhered to one another For each sample edge, apparent separation between adjacent sheet layers is identified by naked eye observation and the length of the apparent edge separation is measured by using a ruler. The percentage of adhesion is then calculated as follows: Length of apparent edge separation summed across the four edges (centimeters)/the sum of the four edge lengths (centimeters). A minimum of 3 repeat measurements for drop test is carried out for each formulation.

Test 12: Stability of the Bleaching Agent

The stability of the bleaching agent within the solid article is determined as the level of available oxygen (AvO) in the solid article after a period of storage. Particularly, the level of AvO is determined by an iodometric titration analysis. The samples are acidified with glacial acetic acid, which is followed by the addition of excess potassium iodide. The peroxide ($H_2O_2$) in reaction [1] quantitatively oxidizes the iodide ($I^-$) to iodine ($I_2$). The iodine [2] complexes with the excess iodide to form a water-soluble triiodide species ($I_3^-$). The concentration of triiodide is determined by titration with sodium thiosulfate [3] and is proportional to the amount of available oxygen in the sample.

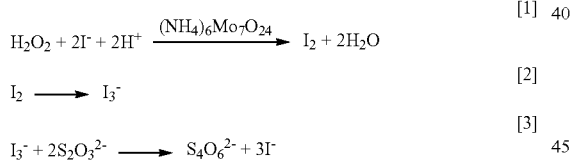

[1]

$$H_2O_2 + 2I^- + 2H^+ \xrightarrow{(NH_4)_6Mo_7O_{24}} I_2 + 2H_2O$$

[2]

$$I_2 \longrightarrow I_3^-$$

[3]

$$I_3^- + 2S_2O_3^{2-} \longrightarrow S_4O_6^{2-} + 3I^-$$

Operations

1. Weigh, to an accuracy of 0.001 g, the entire contents of sample into a 1 L volumetric flask. Record weight as Wg.
2. Carefully dilute with 10% acetic acid.
3. Bring to volume with 10% acetic acid. Stir well for approximately 2 hrs.
4. Pipet 10 ml into a titration vessel while maintaining stirring. Then add 40 mL of 10% acetic acid to the vessel.
5. Add 10 mL of 40% potassium iodide solution to the titration vessel and 1 ml of molybdate reagent to accelerate the reaction.
6. Begin titrating with 0.1 N sodium thiosulfate solution. Titrate quickly.
7. Titrate slowly until the solution becomes colorless and remains without color for at least 10 seconds, assuming reach endpoint.
8. Record the volume to reach the endpoint as T mL.

Calculation $$\% \, AvO = \frac{T * 0.1 * 0.8 * 1000}{W * 10}$$

Test 13: Viscosity

The viscosity values of liquid composition are measured using a Malvern Kinexus Lab+rheometer with cone and plate geometry (CP1/50 SR3468 SS), a gap width of 0.054 mm, a temperature of 20° C. and a shear rate of 1.0 reciprocal seconds for a period of 360 seconds.

Test 14: Anti-Microorganism Effect

The anti-microorganism effect of the solid sheets according to the present disclosure is measured in accordance with the simulation method of Chinese Light Industry Standard QB/T 2738-2012 (Test methods for evaluating daily chemical products in antibacterial and bacteriostatic efficacy). Briefly, under simulated laundry conditions, sets of inoculated fabric swatches are placed into diluted product solution and agitated. After a specified contact time, the wash water and the test fabric are individually cultured quantitatively to determine. Particularly, *Staphylococcus aureus* and *Escherichia coli* are used as test strains. The killing efficacy is calculated as follows:

Killing %=$(I-II)/I \times 100$ where I is the average number of colonies for the control sample;

II is the average number of colonies for the test sample.

Examples

Example 1: Different OCF Structures in Solid Sheet Made by Different Heating/Drying Arrangements Wet pre-mixtures with the following surfactant/polymer compositions as described in Table 1 and Table 2 below were prepared, for laundry care and hair care sheets, respectively.

TABLE 1

| (LAUNDRY CARE FORMULATION) | | |
|---|---|---|
| Materials: | (Wet) w/w % | (Dry) w/w % |
| Polyvinyl alcohol (with a degree of polymerization of about 1700) | 7.58 | 21 |
| Glycerin | 1.08 | 3 |
| Linear Alkylbenzene Sulfonate | 19.12 | 53 |
| Sodium Laureth-3 Sulfate | 3.61 | 10 |
| C12-C14 Ethoxylated alcohol | 3.61 | 10 |
| Water | Balance | Balance |

Viscosity of the wet pre-mixture composition as described in Table 1 was about 14309.8 cps. After aeration, the average density of such aerated wet pre-mixture was about 0.25 g/cm³.

TABLE 2

(HAIR CARE FORMULATION-SHAMPOO)

| Materials: | (Wet) w/w % | (Dry) w/w % |
|---|---|---|
| Polyvinyl alcohol (with a degree of polymerization of about 1700) | 6.85 | 23.69 |
| Glycerin | 2.75 | 9.51 |
| Sodium Lauryl Sulfate | 9.52 | 32.89 |
| Sodium Laureth-3 Sulfate | 3.01 | 10.42 |
| Sodium Lauroamphoacetate | 5 | 17.28 |
| Citric acid (anhydrous) | 0.93 | 3.21 |
| Water | Balance | Balance |

Viscosity of the wet pre-mixture composition as described in Table 2 was about 19254.6 cps. After aeration, the average density of such aerated wet pre-mixture was about 0.225 g/cm³.

Flexible, porous, dissolvable solid Sheets A and B were prepared from the above wet pre-mixtures as described in Tables 1 and 2 using a continuous aerator (Aeros) and a rotary drum drier, with the following settings and conditions as described in Table 3 below:

TABLE 3

(DRUM DRYING)

| Parameters | Value |
|---|---|
| Wet pre-mixture temperature before and during aeration | 80° C. |
| Aeros feed pump speed setting | 600 |
| Aeros mixing head speed setting | 500 |
| Aeros air flow rate setting | 100 |
| Wet pre-mixture temperature before drying | 60° C. |
| Rotary drum drier surface temperature | 130° C. |
| Rotary drum drier rotational speed | 0.160 rpm |
| Drying time | 4.52 min |

A flexible, porous, dissolvable solid Sheet C was also prepared from the above wet pre-mixture as described in Table 2 using a continuous aerator (Oakes) and a mold placed on a hot plate (which provides bottom conduction-based heating), with the following settings and conditions as described in Table 4 below:

TABLE 4

(HOT PLATE DRYING)

| Parameters | Value |
|---|---|
| Wet pre-mixture temperature before and during aeration | 80° C. |
| Oakes air flow meter setting | 19.2 L/hour |
| Oakes pump meter speed setting | 20 rpm |
| Oakes mixing head speed | 1500 rpm |
| Mold depth | 1.0 mm |
| Hot plate surface temperature | 130° C. |
| Drying time | 12.5 min |

Further, flexible, porous, dissolvable solid Sheets I and II were prepared from the above wet pre-mixtures described in Tables 1 and 2 using a continuous aerator (Oakes) and a mold placed on an impingement oven, with the following settings and conditions as described in Table 5 below:

TABLE 5

(IMPINGEMENT OVEN DRYING)

| Parameters | Value |
|---|---|
| Wet pre-mixture temperature before and during aeration | 80° C. |
| Oakes air flow meter setting | 19.2 L/hour |
| Oakes pump meter speed setting | 20 rpm |
| Oakes mixing head speed | 1500 rpm |
| Mold depth | 1.0 mm |
| Impingement oven temperature | 130° C. |
| Drying time | 6 min |

Tables 6-9 as follows summarize various physical parameters and pore structures measured for the solid Sheets A-C and solid Sheets I-II made from the above-described wet pre-mixtures and drying processes.

TABLE 6

(PHYSICAL PARAMETERS)

| Sheet Samples | Formulation | Drying Process | Average Basis Weight g/m² | Average Density g/cm³ | Average Thickness mm | Specific Surface Area m²/g |
|---|---|---|---|---|---|---|
| A | Laundry Care | Rotary Drum | 147.5 | 0.118 | 1.265 | 0.115 |
| B | Hair Care | Rotary Drum | 138.4 | 0.111 | 1.254 | 0.107 |
| C | Hair Care | Hot Plate | 216.3 | 0.111 | 1.968 | — |
| I | Laundry Care | Impingement Oven | 116.83 | 0.118 | 1.002 | — |
| II | Hair Care | Impingement Oven | 212.9 | 0.111 | 1.929 | — |

TABLE 7

(OVERALL PORE STRUCTURES)

| Sheet Samples | Formulation | Drying Process | Percent Open Cell Content % | Overall Average Pore Size μm | Average Cell Wall Thickness μm |
|---|---|---|---|---|---|
| A | Laundry Care | Rotary Drum | 90.75 | 467.1 | 54.3 |
| B | Hair Care | Rotary Drum | 93.54 | 466.9 | 42.8 |
| C | Hair Care | Hot Plate | — | 287.4 | 19.7 |
| I | Laundry Care | Impingement Oven | — | 197.6 | 15.2 |
| II | Hair Care | Impingement Oven | — | 325.1 | 18.7 |

TABLE 8

(SURFACE AND REGIONAL PORE STRUCTURES)

| Sheet Samples | Formulation | Drying Process | Surface Average Pore Diameter (μm) Top | Average Pore Size (μm) | | |
|---|---|---|---|---|---|---|
| | | | | Top | Middle | Bottom |
| A | Laundry Care | Rotary Drum | 201.5 | 458.3 | 479.1 | 463.9 |
| B | Hair Care | Rotary Drum | 138.2 | 412.4 | 519.0 | 469.1 |
| C | Hair Care | Hot Plate | 120.8 | 259.7 | 292.0 | 309.9 |
| I | Laundry Care | Impingement Oven | 53.3 | 139.9 | 213.1 | 238.7 |
| II | Hair Care | Impingement Oven | 60.0 | 190.7 | 362.6 | 419.6 |

TABLE 9

(VARIATIONS BETWEEN REGIONAL PORE STRUCTURES)

| Sheet Samples | Formulation | Drying Process | Cross-Region Relative STD (%) | Btw-Region Ratios of Average Pore Sizes | | |
|---|---|---|---|---|---|---|
| | | | | Bottom-to-Top | Bottom-to-Middle | Middle-to-Top |
| A | Laundry Care | Rotary Drum | 2.31% | 1.012 | 0.968 | 1.046 |
| B | Hair Care | Rotary Drum | 11.43% | 1.137 | 0.904 | 1.259 |
| C | Hair Care | Hot Plate | 8.84% | 1.193 | 1.061 | 1.124 |
| I | Laundry Care | Impingement Oven | 25.99% | 1.706 | 1.120 | 1.523 |
| II | Hair Care | Impingement Oven | 36.74% | 2.200 | 1.157 | 1.901 |

Figure 6B:
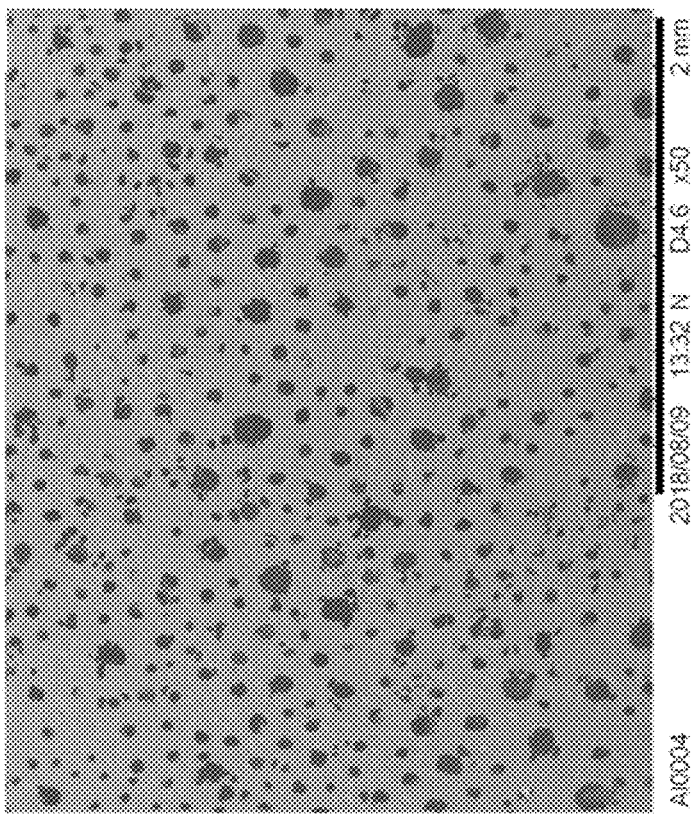
FIG. 6B shows a SEM image of the top surface of an alternative flexible, porous, dissolvable sheet containing the same fabric care actives as the sheet shown in FIG. 6A, but which is made by a process employing an impingement oven-based heating/drying arrangement.
Figure 6A:
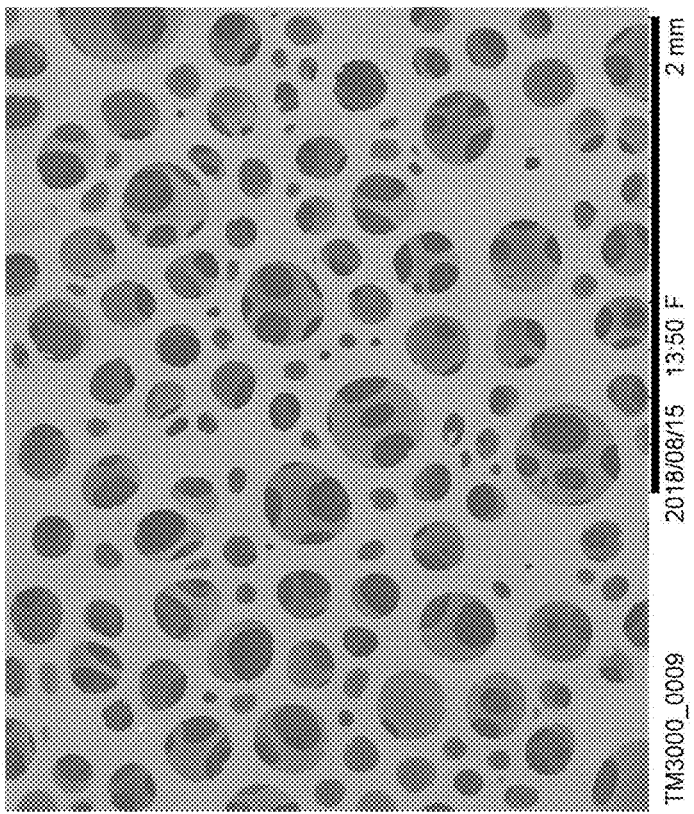
FIG. 6A shows a Scanning Electron Microscopic (SEM) image of the top surface of a flexible, porous, dissolvable sheet containing fabric care actives, which is made by a process employing a rotary drum-based heating/drying arrangement.

The above data demonstrates that the solid sheets as being predominantly open-celled and that the solid sheets made by the rotary drum-drying process have Top Surface Average Pore Diameters of greater than 100 μm, while the solid sheets made by the impingement oven process do not. Specifically, FIG. 6A shows a Scanning Electron Microscopic (SEM) image of the top surface of the Sheet A, while FIG. 6B shows a SEM image of the top surface of the solid Sheet I.

Further, the above data demonstrates that the solid sheets made by the rotary drum-drying process have significantly less regional variations in their Average Pore Sizes than the solid sheets made by the impingement oven process, especially with significantly smaller ratios of the bottom Average Pore Size over the top Average Pore Size.

Example 2: Stable Coating Compositions Obtained by Adding a Thickener

Coating compositions comprising a liquid carrier, solid particles and a thickener as well as coating compositions comprising only a liquid carrier and solid particles were prepared and then tested in accordance with Test 10: Stability of Coating Composition. The results are shown in the table below. The addition of a thickener into a liquid carrier containing a non-ionic surfactant successfully achieves a stable coating composition.

TABLE 10

| # | Solid | Solid wt % | Liquid carrier | Liquid carrier wt % | Thickener | Thickener wt % | Result |
|---|---|---|---|---|---|---|---|
| Group 1: Different solid particles thicker vs. w/o thickener) ||||||||
| 1 | Percarbonate[1] | 40.0 | Non-ionic surfactant[2] | 60.0 | N/A | N/A | Unstable |
| 2 | Percarbonate | 40.0 | Non-ionic surfactant | 58.0 | Silica[3] | 2.0 | Stable |
| 3 | TAED[4] | 50.0 | Non-ionic surfactant | 50.0 | N/A | N/A | Unstable |
| 4 | TAED | 50.0 | Non-ionic surfactant | 48.0 | Silica | 2.0 | Stable |
| 5 | Anionic surfactant A[5] | 20.0 | Non-ionic surfactant | 80.0 | Silica | 0.0 | Unstable |
| 6 | Anionic surfactant A | 20.0 | Non-ionic surfactant | 79.0 | Silica | 1.0 | Stable |
| 7 | Anionic and Amphoteric surfactant B[6] | 20.0 | Non-ionic surfactant | 80.0 | N/A | N/A | Unstable |
| 8 | Anionic and Amphoteric surfactant B | 20.0 | Non-ionic surfactant | 79.0 | Silica | 1.0 | Stable |
| Group 2: Different thickeners ||||||||
| 9 | Percarbonate | 60.0 | Non-ionic surfactant | 39.0 | Xanthan Gum | 1.0 | Unstable |
| 10 | Percarbonate | 60.0 | Non-ionic surfactant | 39.5 | Silica | 0.5 | Stable |

[1] Percarbonate sodium (SPC) available from Jinke.
[2] C12-C14 Ethoxylated alcohol (AE7).
[3] Aerosil A200 available from Evonik Industries.
[4] TAED (96% active) available from Jinke.
[5] Linear Alkylbenzene Sulfonate (LAS), 80% active
[6] Sodium Laureth-3 Sulfate (AES) together with Amine Oxide (75.2% AES and 18.8% AO)

Example 3: Improved Leakage of the Coating Composition with a Thickener Compared to the Coating Composition without a Thickener Dissolvable solid articles containing the coating compositions were prepared as follows.

Firstly, large solid sheets (with minimum area 1.0×1.0 m) were prepared according to the method in the Section III: PROCESS OF MAKING SOLID SHEETS.

Specifically, a wet pre-mixture containing the ingredients of solid sheets and additional water was first prepared, to result in a total solids content of about 35% by weight (i.e., the total water content in the slurry is about 65% by weight). The method of slurry preparation was as follows:
1. Water and glycerin were firstly added together into a glass beaker and stirred at 200 rpm using an overhead stirrer.
2. While continuing to stir, the polyvinyl alcohol was then slowly added into the beaker containing water and glycerin, ensuring that no foaming of the solution or clumping of the polyvinyl alcohol occurred.
3. The beaker was then placed in a water bath and heated to 80° C. while continuing stirring. The beaker was covered with clingfilm or tinfoil in order to mitigate water evaporation and left to continue mixing for at least 1.0 hour.
4. The remaining components were weighed and added together in a separate glass beaker. The balance of water required to achieve 65% total water content in the slurry was also added to this beaker.
5. This beaker was placed in a water bath at 80° C., and its contents were stirred using an overhead stirrer at 500 rpm for at least 30 minutes.
6. Once the predefined mixing time was reached in both beakers, the contents of both were added together into a single glass beaker, followed by continued stirring at 500 rpm and the temperature was maintained at 80° C. for at least another 30 minutes.

The wet pre-mixture was then aerated as follows:
1. An Aeros A20 continuous aerator, consisting of a jacketed hopper (model JCABT10) and A20 mixing head, was preheated to 80° C. using a water bath and pump.
2. The slurry prepared previously was then added to the hopper. The aerator unit was then switched on and the mixing head speed, feed pump speed, and air flow rates were set to 600, 500 and 100 respectively.
3. The aerated slurry was collected from the aerator outlet and its density measured by filling a density cup of known volume and weighing the mass of the aerated slurry. At the aerator settings described above, an aerated slurry density of about 0.225 g/cm$^3$ was achieved.

Flexible and porous solid sheets of about 0.8-1.5 mm in thickness were produced using a rotary drum dryer process, as follows:
1. The rotary drum dryer (having a drum diameter of about 1.5 m) is pre-heated to about 100° C.
2. The aerated slurry collected from the Aeros A20 outlet is added to the feeding trough of the drum dryer.
3. Once added, the rotation of the drum dryer starts and is set at a rotating speed so that the slurry residence time on the heated drum is about 15 minutes.
4. Once dried, the flexible and porous sheets so formed are peeled from the drum surface and placed in a plastic bag.

Then, the solid sheets were stored under ambient relative humidity of 41 to 45% and temperature of 23 to 24.5° C. for a minimum of 1 hour.

10×10 cm square samples of solid sheets were then cut out from the larger sheets by utilizing a paper guillotine. All four edges of the 10×10 cm square were cut by utilizing the paper guillotine. None of the existing edges of the larger sheet stack were used as edges of the smaller 10×10 cm square.

The coating composition was then added to the center of one of the 10×10 cm square samples according to Coating Method as described below, and a second 10×10 cm sample then placed on top of the first sample, such that the two sheet layers were orientated in toe-to-toe configuration. No excessive pressure was applied to the sheet stack during the testing, wherein the excessive pressure is defined as any pressure resulting in a 0.05 mm or greater thickness change of the sheet. The 10×10 cm sample was further cut by using the paper guillotine to a smaller 5×5 cm sample, in which the coating composition was remained in the center of the 5×5 cm sample. Then, the 5×5 cm samples were used in the leakage test.

The Coating Method comprised the following steps. Particularly, the coating composition was obtained by mixing the ingredients. Then, a pipette or a spoon was employed to dispense droplets of the coating composition onto a single location on the surface of the solid sheets, in which a pipette was used if the coating composition was a mixture of liquid and solid particles and has a good flowability. This location was always the centermost point of the total foam mass. With the solid sheet placed on a mass balance and the mass tared to zero, the droplets were continuously added until the required mass of coating composition was achieved.

Particularly, the solid sheet and coating compositions as used in this example comprise ingredients as shown in Table 11 and 12, respectively. Samples 11 to 17 comprise the same solid sheets but different coating compositions. More particularly, Sample 14 comprises a coating composition in the form of solid particles only in which 1.8 grams of percarbonate powder were added which equals the total mass of percarbonate powder added in Sample 13. Sample 17 was solid sheets without a coating composition.

TABLE 11

| Ingredients | w/w % by weight of the solid sheet (Dry) |
|---|---|
| Polyvinyl Alcohol[1] | 20% |
| C10-16 Alkyl Ether Sulfate | 43.9% |
| Glycerin | 9.0% |
| Amine Oxide | 9.9% |
| Ethoxylated Polyethyleneimine | 2.0% |
| Soap Powder | 2.0% |
| Zeolite | 1.0% |
| Water | 7.0% |
| Perfume Microcapsule | 5.0% |
| Miscellaenous | Q.S. |

[1]Polyvinyl alcohol having a hydrolysis level of 88% and a degree of polymerization of about 1700, available from Sigma Aldrich.

TABLE 12

| # | Solid | Solid wt % | Liquid carrier | Liquid carrier wt % | Thickener | Thickener wt % | Coating composition added, grams* | Score |
|---|---|---|---|---|---|---|---|---|
| 11 | Percarbonate[1] | 40.0 | Non-ionic surfactant[2] | 60.0 | N/A | N/A | 3.0 | 2 |
| 12 | Percarbonate | 40.0 | Non-ionic surfactant | 58.0 | Silica[3] | 2.0 | 3.0 | 5 |
| 13 | Percarbonate | 60.0 | Non-ionic surfactant | 39.5 | Silica | 0.5 | 3.0 | 5 |
| 14 | Percarbonate | 100.0 | N/A | N/A | N/A | N/A | 1.8[4] | 0 |
| 15 | Anionic surfactant A[5] | 20.0 | Non-ionic surfactant | 79.0 | Silica | 1.0 | 3.0 | 5 |
| 16 | Anionic and Amphoteric surfactant B[6] | 20.0 | Non-ionic surfactant | 79.0 | Silica | 1.0 | 3.0 | 5 |
| 17 | N/A | N/A | N/A | N/A | N/A | N/A | 0.0[7] | 5 |

[1]Percarbonate sodium (SPC) available from Jinke.
[2]C12-C14 Ethoxylated alcohol (AE7).
[3]Aerosil A200 available from Evonik Industries.
[4]Solid particles only (no liquid carrier or thickener)
[5]Linear Alkylbenzene Sulfonate (LAS), 80% active
[6]Sodium Laureth-3 Sulfate (AES) together with Amine Oxide (75.2% AES and 18.8% AO)
[7]Foam sheets only without a coating composition.

The leakage of the foam sheets containing the coating compositions therebetween were tested in accordance with Test 11: Leakage of Coating Composition. The results are shown in the table above, indicating that the addition of a thickener significantly improves the leakage of the coating compositions (5 vs. 2 or 0).

Example 4: Anti-Microorganism Effect of Solid Articles Containing the Bleaching Agent Dissolvable solid articles containing the bleaching agent were prepared similarly as in Example 3, in which the solid sheets and the coating composition respectively had the formulation shown in the following tables. Further, half of the solid sheets were firstly stacked in head-to-toe configuration, the coating composition was then dispensed onto the centermost point of the top sheet, and the remaining sheets then stacked on top. With the solid sheet placed on a mass balance and the mass tared to zero, the droplets were continuously added until the required mass of coating composition is achieved. Particularly, the total number of solid sheets is 10 in which 1$^{st}$ to 3$^{rd}$ sheets and 9$^{th}$ to 10$^{th}$ sheets from bottom to top are outer solid sheets of which the formula is shown in Table 13a and 4$^{th}$ to 8$^{th}$ are inner solid sheets of which the formula is shown in Table 13b, and the coating compositions are applied between 5* and 6' sheets from bottom to top. Samples 18 and 19 comprise the same solid sheets but different coating compositions.

TABLE 13a

Outer solid sheets

| Ingredients | w/w % by weight of the solid sheet (Dry) |
| --- | --- |
| Polyvinyl Alcohol[1] | 15.6% |
| C10-16 Alkyl Ether Sulfate | 34.2% |
| TAED | 19.9% |
| Glycerin | 7.1% |
| Amine Oxide | 7.7% |
| Soap Powder | 1.4% |
| Water | 6.0% |
| Perfume | 2.5% |
| Perfume Microcapsule | 3.9% |
| Miscellaenous | Q.S. |

[1]Polyvinyl alcohol having a hydrolysis level of 88% and a degree of polymerization of about 1700, available from Sigma Aldrich.

TABLE 13b

Inner solid sheets

| Ingredients | w/w % by weight of the solid sheet (Dry) |
| --- | --- |
| Polyvinyl Alcohol[1] | 20.0% |
| C10-16 Alkyl Ether Sulfate | 43.9% |
| Glycerin | 9.0% |
| Amine Oxide | 9.9% |
| Ethoxylated Polyethyleneimine | 2.0% |
| Soap Powder | 2.0% |
| Zeolite | 1.0% |
| Water | 7.0% |
| Perfume Microcapsule | 5.0% |
| Miscellaenous | Q.S. |

[1]Polyvinyl alcohol having a hydrolysis level of 88% and a degree of polymerization of about 1700, available from Sigma Aldrich.

TABLE 14

Coating composition

| # | Solid | Solid wt % | Liquid carrier | Liquid carrier wt % | Thickener | Thickener wt % | Mass of sheet/ coating composition (g/g) |
| --- | --- | --- | --- | --- | --- | --- | --- |
| 18 | Percarbonate[1] | 50 | Non-ionic surfactant[2] | 49.5 | Silica[3] | 0.5 | 1.98/3.00 |
| 19 | Percarbonate | 60 | Non-ionic surfactant | 39.5 | Silica | 0.5 | 3.32/3.24 |

[1]Percarbonate sodium (SPC) available from Jinke.
[2]C12-C14 Ethoxylated alcohol (AE7).
[3]Aerosil A200 available from Evonik Industries.

The anti-microorganism effect of the solid articles according to the present disclosure was tested. Particularly, the solid articles were firstly fully dissolved in water and then diluted according to the specified dilution factor. Subsequently, the anti-microorganism effect was determined according to Test 14 (i.e., simulation method in QBT2738-2012) by using a dilution factor of 33. The results shown in the following Table 15 indicate the solid articles according to the present disclosure achieves an excellent anti-microorganism effect.

TABLE 15

| | Dilution Factor | Test strain: S.a NBRC12732 (G+) | Test strain: E.c NBRC3972 (G−) |
| --- | --- | --- | --- |
| Sample 18 | 33 | >99.99% | >99.99% |
| Sample 19 | 33 | >99.999% | >99.99% |

Example 5: Improved Stability of a Bleaching Agent in Coating Compositions Contained in Dissolvable Solid Articles Compared to the Bleaching Agent Alone Stored Under the Same Conditions Dissolvable solid articles containing the coating compositions were prepared similarly as Example 3, in which the coating compositions comprised a bleaching agent. Further, half of the sheets were firstly stacked in head-to-toe configuration, the coating composition was then dispensed onto the centermost point of the top sheet, and the remaining sheets then stacked on top. If more than one coating composition was applied, some of the sheets were firstly stacked in head-to-toe configuration, and a first coating composition was then dispensed onto centermost point of the top sheet. Subsequently, one or more sheets stacked on top and a second coating composition was then dispensed onto centermost point of the top sheet. Finally, the remaining sheets then stacked on top. The sheets were always orientated such that the coating composition was dispensed onto the bottom side of the sheet. With the solid sheet placed on amass balance and the mass tared to zero, the droplets were continuously added until the required mass of coating composition is achieved.

The solid sheets and the coating compositions respectively have the formulation shown in the following table in which the Comparative Example i is a simple mixture of percarbonate particles and TAED particles. Further, the total number of solid sheet layers of Examples I and II are 15 in which the first coating composition are applied between $5^{th}$ and $6^{th}$ sheets from bottom to top and the second coating composition are applied between $10^{th}$ and $11^{th}$ sheets from bottom to top.

TABLE 16

| Materials (Dry) wt % by total weight of the solid article | Example I | Example II | Compar. Example i |
|---|---|---|---|
| Sheet (15 layers in total) | | | |
| Polyvinyl alcohol[1] | 6.60 | 9.50 | — |
| Glycerin | 4.00 | 14.40 | — |
| Linear Alkylbenzene Sulfonate | 14.20 | — | — |
| Sodium Laureth-3 Sulfate | 4.10 | — | — |
| Ethoxylated Polyethyleneimine | 0.60 | — | — |
| DEEDMAC[2] | — | 9.70 | — |
| Potato starch | — | 1.30 | — |
| Palm kernel fatty acid soap powder | 0.60 | — | — |
| Sodium Aluminosilicate (crystalline)/Zeolite | 0.30 | — | — |
| Format | Solid sheet | Solid sheet | — |
| First Coating Composition (applied between 5th and 6th sheets from bottom to top) | | | |
| C12-C14 Ethoxylated alcohol | 13.25 | 11.15 | — |
| Percarbonate[3] | 20.40 | 20.40 | 60.00 |
| Silica[4] | 0.15 | 0.25 | — |
| Format | Viscous Liquid | Viscous Liquid | Particles |
| Second Coating Composition (applied between 10th and 11th sheets from bottom to toe) | | | |
| C12-C14 Ethoxylated alcohol | 13.25 | 11.15 | — |
| TAED[5] | 13.70 | 12.90 | 36.80 |
| Perfume | 2.40 | 2.30 | — |
| Silica[6] | 0.15 | 0.25 | — |
| Chelant (DTPA) | 2.20 | 2.10 | — |
| Brightener | 0.30 | 0.30 | — |
| Format | Viscous liquid | Viscous liquid | Particles |
| Water and Miscellaneous | Balance | Balance | Balance |
| TOTAL | 100 | 100 | 100 |

[1]Polyvinyl alcohol having a hydrolysis level of 88% and a degree of polymerization of about 1700, available from Sigma Aldrich.
[2]Rewoquat Ci-Deedmac (Cationic surfactant) from Evonik
[3]Percarbonate sodium (SPC) available from Jinke.
[4]Aerosil A200 available from Evonik Industries.
[5]TAED (96% active) available from Jinke.
[6]Aerosil A200 available from Evonik Industries.

The stability of bleaching agents contained in the solid articles according to the present disclosure was tested according to Test 12. The results shown in the following Table 17 indicate a significant improvement in the stability of bleaching agents contained in the solid articles compared to the bleaching agents alone.

TABLE 17

| | Example I | Example II | Compar. Example i |
|---|---|---|---|
| Average sample mass, g | 17.65 | 17.60 | 6.04 |
| Average available oxygen recovery after three-week storage [1], % | 88.6 | 87.1 | 79.1 |

[1] Sealed in a 45 micron thick PP sachet and then stored under 45° C., 75% RH for three weeks.

Prior to the present invention, it was expected that the porous structure of the solid sheet according to the present disclosure may compromise the stability of bleaching agents or at most remain similar stability with that outside the solid sheet according to the present disclosure, because the porous structure may absorb much moisture in the environment and the moisture may react with the bleaching agents. On the contrary, it is surprisingly discovered by the inventors that the stability of bleaching agents loaded in the dissolvable solid article is significantly improved compared to the bleaching agents alone.

The moisture inside (i.e., the sample was obtained at the centermost of the layer that is in contact with the 1st coating composition) and at the edge of (i.e., the sample was obtained at the edge of solid sheets) the solid sheets of Example I was tested according to Test 4 after storage for 24 hours (sealed in a 45 micron thick PP sachet and then stored under 45° C., 75% RH). The results shown in the following Table 18 indicate the moisture inside and at the edge of the solid sheets are substantially the same at 24 hours after the solid sheets are placed in a humid environment. Therefore, the improved stability achieved in the present disclosure is completely unexpected, because the bleaching agent in the solid sheets can still come into contact with the moisture.

TABLE 18

| | Inside of the solid sheet | At the edge of the solid sheet |
|---|---|---|
| Moisture (at 24 hours) | 12.92% | 13.02% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable solid article comprising two or more flexible, porous, dissolvable sheets, wherein each of said two or more sheets comprises a water-soluble polymer and a surfactant and is characterized by a Percent Open Cell Content of from about 80% to about 100% and an Overall Average Pore Size of from about 100 μm to about 2000 μm; and a coating composition comprising a non-aqueous liquid carrier, solid particles, and a thickening agent, wherein said composition comprises: a) from about 20% to about 80%, of said non-aqueous liquid carrier by total weight of said coating composition; b) from about 20% to about 60%, of said solid particles by total weight of said coating composition; c) from about 0.1% to about 5%, of said thickening agent by total weight of said coating composition; wherein said non-aqueous liquid carrier comprises a non-ionic surfactant, said solid particles comprise a bleaching agent, a bleach activator, or an anionic surfactant, said thickening agent comprises silica; and wherein said coating is present on at least one surface of at least one of said two or more sheets, provided that said coating composition is not on any of the outer surfaces of the dissolvable solid article.

2. The dissolvable solid article of claim 1, wherein said non-aqueous liquid carrier further comprises polyethylene glycol, polypropylene glycol, silicone, fatty acid, perfume oil, an organic solvent, or a combination thereof.

3. The dissolvable solid article of claim 1, wherein said non-ionic surfactant comprises a $C_6$-$C_{20}$ linear or branched alkylalkoxylated alcohol having a weight average degree of alkoxylation ranging from about 5 to about 15.

4. The dissolvable solid article of claim 1, wherein said thickening agent further comprises a clay, a polyacrylate thickener, a polyacrylamide thickener, an alginate, an ethoxylated cellulose, a hydroxy propyl cellulose, a hydroxy ethyl cellulose, or a combination thereof.

5. The dissolvable solid article of claim 1, wherein said solid particles further comprise an oxidative dye compound, a pH modifier, a buffering agent, a radical scavenger, a chelant, a warming active, a color indicator, an anionic surfactant, an enzyme, an effervescent system, or a combination thereof.

6. The dissolvable solid article of claim 5, wherein said anionic surfactant comprises alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, or a combination thereof;
wherein said enzyme comprises proteases, amylases, cellulases, lipases, xylogucanases, pectate lyases, mannanases, cutinases, or a combination thereof; and
wherein said effervescent system is an acid source comprising citric acid, malic acid, tartaric acid, fumaric acid, adipic acid, maleic acid, aspartic acid, glutaric acid, malonic acid, succinic acid, boric acid, benzoic acid, oleic acid, citramalic acid, 3-chetoglutaric acid, or any combination thereof, and an alkali source comprising a carbonate salt, a bicarbonate salt, a sesquicarbonate salt, or a combination thereof.

7. The dissolvable solid article of claim 1, wherein said solid particles comprise C6-C20 linear alkylbenzene sulphonate surfactant.

8. The dissolvable solid article of claim 1, wherein said solid particles comprise a bleaching agent selected from the group consisting of percarbonate salts, perborate salts, persulfate salts, or any combination thereof.

9. The dissolvable solid article of claim 1, wherein said solid particles comprise a bleach activator.

10. The dissolvable solid article of claim 9, wherein the bleach activator comprises tetraacetylethylenediamine, oxybenzene sulphonate, caprolactam; pentaacetate glucose, nitrile quaternary ammonium, imide bleach activator, or a combination thereof.

11. The dissolvable solid article according to claim 1, wherein the coating composition comprises from about 0.15% to about 2%, of said thickening agent by total weight of said coating composition.

12. The dissolvable solid article of claim 1, wherein said coating composition comprises:

1) From about 20% to about 60%, of said non-aqueous liquid carrier by total weight of said coating composition;
2) From about 30% to about 60%, of said solid particles by total weight of said coating composition;
3) From about 0.1% to about 3%, of said thickening agent by total weight of said coating composition.

13. The dissolvable solid article of claim 1, wherein at least one of said sheets comprises from about 9% to about 40%, of said water-soluble polymer by total weight of said sheet;
wherein said water-soluble polymer has a weight average molecular weight of from about 20,000 to about 150,000 Daltons; and
wherein said water-soluble polymer is a polyvinyl alcohol characterized by a degree of hydrolysis ranging from about 70% to about 90%.

14. The dissolvable solid article of claim 1, wherein at least one of said sheets comprises from about 40% to about 80%, of said surfactant by total weight of said sheet;
wherein said surfactant comprises a $C_6$-$C_{20}$ linear alkylbenzene sulfonate, a $C_6$-$C_{20}$ linear or branched alkylalkoxy sulfates having a weight average degree of alkoxylation ranging from about 0.5 to about 10, a $C_6$-$C_{20}$ linear or branched alkylalkoxylated alcohol having a weight average degree of alkoxylation ranging from about 5 to about 15, a $C_6$-$C_{20}$ linear or branched alkyl sulfate, or a combination thereof.

15. The dissolvable solid article of claim 1, wherein said two or more sheets comprises a first group of sheets and a second group of sheets in which the coating composition is present on at least one surface of at least one of said first group of sheets but not on any one surface of said second group of sheets.

16. The dissolvable solid article of claim 15, wherein said coating composition comprises a bleaching agent selected from the group consisting of a percarbonate salt, a perborate salt, a persulfate salt, or a combination thereof; and
wherein each sheet within said second group of sheets comprises a bleach activator comprising tetraacetylethylenediamine, oxybenzene sulphonate, caprolactam; pentaacetate glucose, nitrile quaternary ammonium, imide bleach activator, or a combination thereof.

17. A process for preparing a dissolvable solid article according to claim 1 comprising:
providing the two or more flexible, porous, dissolvable sheets and the coating composition;
applying the coating composition on at least one surface of at least one sheet from said two or more sheets; and
arranging the two or more sheets into a stack to form the dissolvable solid article so that the coating composition is not on any of the outer surfaces of the stack.

18. The process of claim 17, wherein said two or more flexible, porous, dissolvable sheets are provided by using the following steps:
a) preparing a wet pre-mixture comprising said water-soluble polymer and said surfactant;
b) aerating said wet pre-mixture to form an aerated wet pre-mixture;
c) forming said aerated wet pre-mixture into a sheet having opposing first and second sides; and
d) drying said formed sheet to make said two or more flexible, porous, dissolvable sheet.

19. The process of claim 18, wherein step d) is conducted for a duration from about 10 min to about 120 min, at a temperature from about 70° C. to about 200° C., along a heating direction that forms a temperature gradient decreasing from the first side to the second side of the formed sheet, wherein the heating direction is substantially opposite to the gravitational direction for more than half of the drying time.

20. The process of claim 19, wherein the wet pre-mixture has a viscosity of from 1,000 cps to 25,000 cps measured at 40° C. and 1 $s^{-1}$, and/or the aerated wet pre-mixture has a density of from about 0.2 g/ml to about 0.6 g/ml.

* * * * *